US009377850B2

(12) United States Patent
Norieda et al.

(10) Patent No.: US 9,377,850 B2
(45) Date of Patent: *Jun. 28, 2016

(54) INPUT DEVICE, INPUT METHOD AND MEDIUM

(75) Inventors: Shin Norieda, Tokyo (JP); Hideo Mitsuhashi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 801 days.

This patent is subject to a terminal disclaimer.

(21) Appl. No.: 13/634,767

(22) PCT Filed: Mar. 14, 2011

(86) PCT No.: PCT/JP2011/055889
§ 371 (c)(1),
(2), (4) Date: Sep. 13, 2012

(87) PCT Pub. No.: WO2011/115035
PCT Pub. Date: Sep. 22, 2011

(65) Prior Publication Data
US 2013/0013229 A1   Jan. 10, 2013

(30) Foreign Application Priority Data

Mar. 15, 2010  (JP) ................................. 2010-057939
Dec. 15, 2010  (JP) ................................. 2010-279667

(51) Int. Cl.
*G06F 3/01*   (2006.01)
*G01N 29/04*   (2006.01)
(Continued)

(52) U.S. Cl.
CPC *G06F 3/011* (2013.01); *G06F 3/01* (2013.01);
*G01H 1/00* (2013.01); *G01H 1/08* (2013.01);
*G01N 29/04* (2013.01); *G01N 29/14* (2013.01)

(58) Field of Classification Search
CPC ............ G01H 1/00; G01H 1/08; G06F 3/011;
G06F 3/01; G06F 3/001; G01N 29/04; G01N 29/14
USPC ...................................... 702/56; 73/584, 1.82
See application file for complete search history.

(56) References Cited

U.S. PATENT DOCUMENTS 6,965,842 B2    11/2005   Rekimoto
8,421,634 B2 *   4/2013   Tan et al. ................... 340/573.1
(Continued)

FOREIGN PATENT DOCUMENTS

CN          1425973 A     6/2003
CN          101008872 A   8/2007
(Continued)

OTHER PUBLICATIONS

Tetsuo Nozawa, "Human skin to the touch panel, developed by Microsoft Carnegie Mellon University", Tech On!, Nikkei BP, Mar. 6, 2010, [online] <http://techon.nikkeibp.co.jp/article/NEWS/20100306/180875/>.

(Continued)

*Primary Examiner* — John Breene
*Assistant Examiner* — Lynda Dinh
(74) *Attorney, Agent, or Firm* — Sughrue Mion, PLLC

(57) ABSTRACT

An input device comprises: a detection unit that detects as detection data a vibration that is generated by tapping on a body of a user and transmitted through the body of the user; and an input information identification unit that refers to the detection data and that identifies a tap position based on a fact that the detection data varies according to a length of a vibration transmission path from the tap position to the detection unit.

14 Claims, 23 Drawing Sheets

(51) Int. Cl.
  *G01N 29/14*  (2006.01)
  *G01H 1/08*  (2006.01)
  *G01H 1/00*  (2006.01)

(56) References Cited

U.S. PATENT DOCUMENTS

2004/0243342 A1  12/2004  Rekimoto
2009/0124872 A1  5/2009  Uchiyama et al.
2009/0146848 A1  6/2009  Ghassabian

FOREIGN PATENT DOCUMENTS

| | | |
|---|---|---|
| JP | 02272617 A | 11/1990 |
| JP | 10-051527 A | 2/1998 |
| JP | 10-200610 A | 7/1998 |
| JP | 2002-358149 A | 12/2002 |

OTHER PUBLICATIONS

Communication dated Sep. 25, 2014 from the State Intellectual Property Office of the People's Republic of China in counterpart application No. 201180010099.8.

David, "Skinput", Inventing Interactive, Mar. 3, 2010, [retrieved on Jan. 15, 2015]. Retrieved from the Internet: <http://www.inventinginteractive.com/2010/03/03/skinput/>.

Communication dated Jan. 20, 2015, issued by the Japanese Patent Office in counterpart Japanese application No. 2012-505658.

* cited by examiner

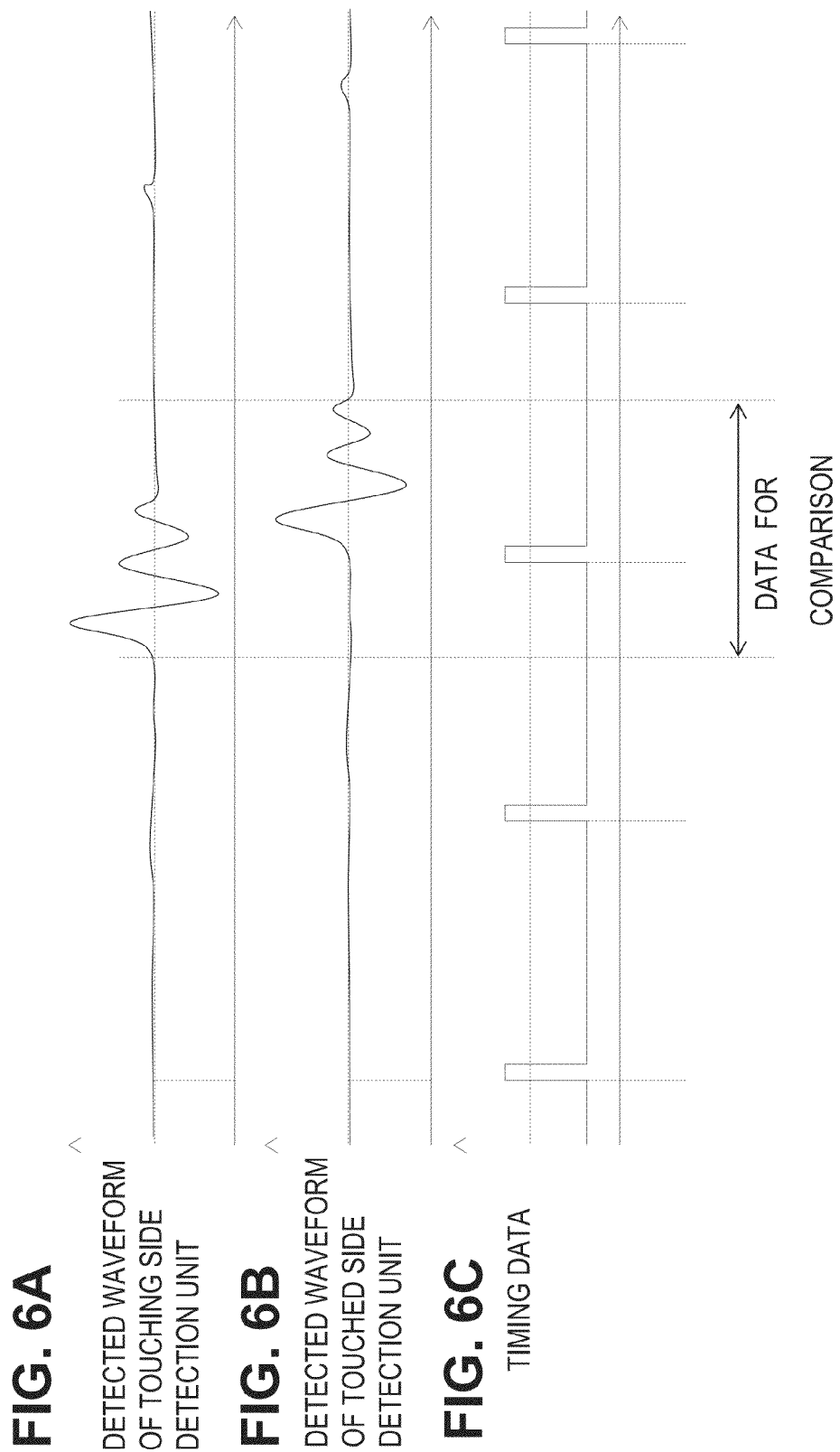

FIG. 9

| | VIBRATION TRANSMISSION TIME AT TOUCHED SIDE DETECTION UNIT | VIBRATION TRANSMISSION TIME AT TOUCHING SIDE DETECTION UNIT | DETECTION TIME DIFFERENCE (TOUCHING SIDE AS THE REFERENCE) |
|---|---|---|---|
| FIRST INPUT AREA | $\dfrac{L_1}{v}$ | | $\dfrac{L_1 - L_0}{v}$ |
| SECOND INPUT AREA | $\dfrac{L_2}{v}$ | $\dfrac{L_0}{v}$ | $\dfrac{L_2 - L_0}{v}$ |
| THIRD INPUT AREA | $\dfrac{L_3}{v}$ | | $\dfrac{L_3 - L_0}{v}$ |

FIG. 11

| INPUT AREA AND ITS FUNCTION | LOWER THRESHOLD | UPPER THRESHOLD |
|---|---|---|
| FIRST INPUT AREA [ SKIP FORWARD ] ▶❙ | −0.00127 | 0.00063 |
| SECOND INPUT AREA [ PLAY / PAUSE ] ▶ | 0.00146 | 0.00216 |
| THIRD INPUT AREA [ STOP ] ■ | 0.00352 | 0.00609 |

DETECTED WAVEFORM
OF TOUCHING SIDE
DETECTION UNIT

DETECTED WAVEFORM
OF TOUCHED SIDE
DETECTION UNIT

FIG. 15

| INPUT AREA AND ITS FUNCTION | LOWER THRESHOLD | UPPER THRESHOLD |
|---|---|---|
| FIRST INPUT AREA<br>[ SKIP FORWARD ] ▶▋ | 1.273 | 1.469 |
| SECOND INPUT AREA<br>[ PLAY / PAUSE ] ▶ | 0.589 | 0.929 |
| THIRD INPUT AREA<br>[ STOP ] ■ | 0.262 | 0.541 |

DETECTED WAVEFORM
OF TOUCHING SIDE
DETECTION UNIT

DETECTED WAVEFORM
OF TOUCHED SIDE
DETECTION UNIT

DETECTED WAVEFORM
OF TOUCHED SIDE
DETECTION UNIT
IN EACH AXIS

X-AXIS
DIRECTION

Y-AXIS
DIRECTION

Z-AXIS
DIRECTION

FIG. 22
| INPUT AREA AND ITS FUNCTION | LOWER THRESHOLD | UPPER THRESHOLD | GRAVITATIONAL ACCELERATION |
|---|---|---|---|
| FIRST INPUT AREA [ SKIP FORWARD ]  | −0.00127 | 0.00063 | (−0.010,−1.010,−8.150) |
| SECOND INPUT AREA [ PLAY / PAUSE ]  | 0.00146 | 0.00216 | (−0.010,−1.010,−8.150) |
| THIRD INPUT AREA [ STOP ]  | 0.00352 | 0.00609 | (−0.010,−1.010,−8.150) |
| FOURTH INPUT AREA [ MUTE ]  | −0.00127 | 0.00063 | (−0.010, 1.010, 8.150) |
| FIFTH INPUT AREA [ VOLUME DOWN ]  | 0.00146 | 0.00216 | (−0.010, 1.010, 8.150) |
| SIXTH INPUT AREA [ VOLUME UP ]  | 0.00352 | 0.00609 | (−0.010, 1.010, 8.150) |
| ⋮ | | | |

INPUT DEVICE, INPUT METHOD AND MEDIUM

REFERENCE TO RELATED APPLICATION

The present application is a National Stage of International Application No. PCT/JP2011/055889 filed Mar. 14, 2011, claiming priority based upon Japanese patent application No. 2010-057939 filed on Mar. 15, 2010 and Japanese patent application No. 2010-279667 filed on Dec. 15, 2010, the contents of all of which are incorporated herein by reference in their entirety. The present invention relates to an input device, input method and medium, and particularly to an input device, input method and medium for a mobile electronic device such as a portable music player and mobile phone.

BACKGROUND

In order to perform an input operation such as adjusting the volume or selecting a song on a small mobile electronic device such as a portable music player, it is necessary to take out the device from a pocket or bag where the device is stored. As a technology for helping the user avoid this action, Patent Document 1 describes a mobile telephone device having parts of its functions attached to an arm.

Further, Patent Document 2 describes a telephone device that is attached to an ear and that performs telephone transmission/reception operation based on a trigger signal generated when the user chews.

Further, Patent Document 3 describes an input apparatus that is configured like a wrist watch and that receives gestures such as "grip," "release," "twist," and "shake" as command input.

Patent Document 1:
Japanese Patent Kokai Publication No. JP-A-10-051527
Patent Document 2:
Japanese Patent Kokai Publication No. JP-A-10-200610
Patent Document 3:
Japanese Patent Kokai Publication No. JP-P2002-358149A

SUMMARY

The entire disclosures of Patent Documents above are incorporated herein in their entirety by reference thereto. The following analysis is given by the present invention.

Regarding the mobile telephone device described in Patent Document 1, since input keys are provided on a compact bracelet-type input device and the input keys are small, it is difficult to locate the input keys and perform an input operation, and input mistakes such as pressing the wrong keys may occur.

Further, regarding the telephone device described in Patent Document 2, since only one type of ON/OFF operation such as chewing action is used to perform input operation, it is difficult to realize the input operation of a plurality of functions that the operated device possesses.

Further, since the input apparatus described in Patent Document 3 uses complex gestures in which complicated movements are combined as an input operation, it is difficult to distinguish between an input operation and ordinary everyday gesture, and an input operation unintended by the user may occur.

Therefore, there is a need in the art to provide an input device, input method, program or medium storing the program that eliminate the need for the user to take out an input device when performing an input operation on a mobile electronic device and simplify the input operation by the user.

According to a first aspect of the present invention, there is provided an input device, comprising:
a detection unit that detects as detection data a vibration that is generated by tapping on a body of a user and transmitted through the body of the user; and
an input information identification unit that refers to the detection data and identifies a tap position based on a fact that the detection data varies according to a length of a vibration transmission path from the tap position to the detection unit.

According to a second aspect of the present invention, there is provided an input method, comprising:
by a computer, detecting as detection data a vibration that is generated by tapping on a body of a user and transmitted through the body of the user; and
referring to the detection data and identifying a tap position based on a fact that the detection data varies according to a length of a vibration transmission path from the tap position to a detection place where the detection data is detected.

According to a third aspect of the present invention, there is provided a program, causing a computer to execute:
detecting as detection data a vibration that is generated by tapping on a body of a user and transmitted through the body of the user; and
referring to the detection data and identifying a tap position based on a fact that the detection data varies according to a length of a vibration transmission path from the tap position to a detection place where the detection data is detected. The program may be stored in a non-transitory computer-readable storage medium.

According to a fourth aspect of the present invention, there is provided an input device, wherein
a detection unit comprises an acceleration sensor and is provided on a wrist on a tapped side, and an input information identification unit identifies an arm posture on a tapped side according to a gravitational acceleration detected by the acceleration sensor and identifies a tap position based on the identified arm posture and on a fact that the detection data varies according to a length of a vibration transmission path from the tap position to the detection unit.

The present invention provides the following advantage, but not restricted thereto. An input device, input method and program relating to the present invention eliminate the need for the user to take out the input device when performing an input operation on a mobile electronic device, and simplify the input operation by the user.

BRIEF DESCRIPTION OF THE DRAWINGS

FIGS. 6A, 6B, and 6C are drawings for explaining vibration waveform extraction performed by the input device relating to the first exemplary embodiment.

FIG. 9 is a table showing the vibration transmission time and detection time difference in each detection unit of the input device relating to the first exemplary embodiment.

FIG. 11 is a table showing an association between lower and upper thresholds and input information identification data in the input device relating to the first exemplary embodiment.

FIG. 15 is a table showing an association between lower and upper thresholds and input information identification data in the input device relating to the second exemplary embodiment.

FIG. 22 is a table showing an association between a combination of lower and upper thresholds and the direction of gravitational acceleration corresponding to the arm posture and input information identification data in the input device relating to the fourth exemplary embodiment.

PREFERRED MODES

Figure 1:
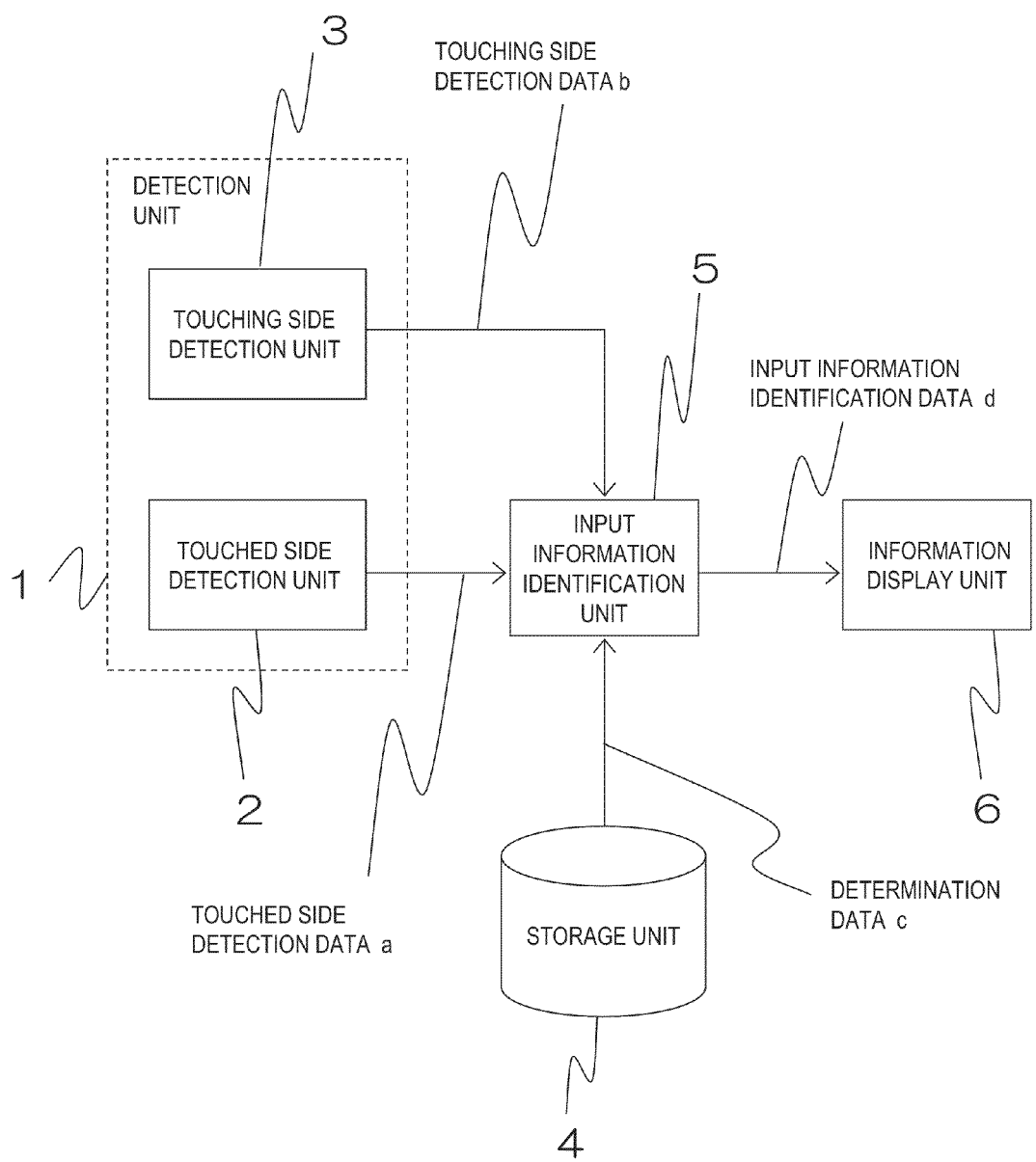
FIG. 1 is a block diagram showing a configuration of an input device relating to a first exemplary embodiment.

In the present disclosure, there are various possible modes, which include the following, but not restricted thereto. According to a first mode, there is provided the input device relating to the first aspect.

According to a second mode, there is provided the input device, wherein the detection unit comprises a first detection unit provided on a tapping side and a second detection unit provided on a tapped side, and the input information identification unit identifies the tap position based on a difference between a time when the first detection unit detects the vibration and a time when the second detection unit detects the vibration.

According to a third mode, there is provided the input device further comprising a storage unit that holds an association between a difference between a time when the first detection unit detects the vibration and a time when the second detection unit detects the vibration, and the tap position, wherein the input information identification unit identifies the tap position by referring to the storage unit.

According to a fourth mode, there is provided the input device, wherein the storage unit holds an association between upper and lower threshold values of a difference between a time when the first detection unit detects the vibration and a time when the second detection unit detects the vibration, and the tap position, and the input information identification unit identifies the tap position by determining whether or not the time difference detected is within a range between the upper and lower threshold values.

According to a fifth mode, there is provided the input device, wherein the detection unit comprises a first detection unit provided on a tapping side and a second detection unit provided on a tapped side, and the input information identification unit identifies the tap position based on a ratio between an amplitude, strength or energy of the vibration detected by the first detection unit and an amplitude, strength or energy of the vibration detected by the second detection unit.

According to a sixth mode, there is provided the input device further comprising a storage unit that holds an association between a ratio between an amplitude, strength or energy of the vibration detected by the first detection unit and an amplitude, strength or energy of the vibration detected by the second detection unit, and the tap position, wherein the input information identification unit identifies the tap position by referring to the storage unit.

According to a seventh mode, there is provided the input device, wherein the storage unit holds an association between upper and lower threshold values of a ratio between an amplitude, strength or energy of the vibration detected by the first detection unit and an amplitude, strength or energy of the vibration detected by the second detection unit, and the tap position, and the input information identification unit identifies the tap position by determining whether or not the ratio of the amplitude, strength or energy of the vibration detected is within a range between the upper and lower threshold values.

According to an eighth mode, there is provided the input device, wherein the detection unit is provided on a tapped side, and the input information identification unit identifies the tap position based on an amplitude, strength or energy of the vibration detected by the detection unit.

According to a ninth mode, there is provided the input method relating to the second aspect.

According to a tenth mode, there is provided a program relating to the third aspect.

According to an eleventh mode, there is provided a non-transitory computer-readable storage medium readable by a computer storing the program.

According to a twelfth mode, in the input device,
the detection unit may comprise an acceleration sensor and may be provided on a wrist on a tapped side, and
the input information identification unit may identify an arm posture on the tapped side according to a gravitational acceleration detected by the acceleration sensor and identify the tap position based on the identified arm posture and on a fact that the detection data varies according to a length of the vibration transmission path from the tap position to the detection unit.

According to the present invention, tapping a part of the body can be assigned to an input operation. Further, according to the present invention, a device that detects input can be a small, bracelet-type device, and the operation by the user to take out the input device in order to perform a device operation can be eliminated. As a result, the complexity associated with input operation can be eliminated, and the time required for input operation can be reduced.

Further, according to the present invention, by assigning input areas to a part of the body of the user such as an arm, sufficiently large input areas can be secured, and an input mistake by the user can be prevented.

Further, according to the present invention, since a plurality of input areas can be assigned, a plurality of types of input operations can be realized and input operations for a plurality of functions possessed by the operated device can be realized.

Further, according to the present invention, since an input operation is triggered by a specific action, which is touching of the body, an input operation and ordinary everyday gesture can be distinguished and an input operation unintended by the user can be avoided.

(First Exemplary Embodiment)

An input device relating to a first exemplary embodiment will be described with reference to the drawings.

Figure 2:
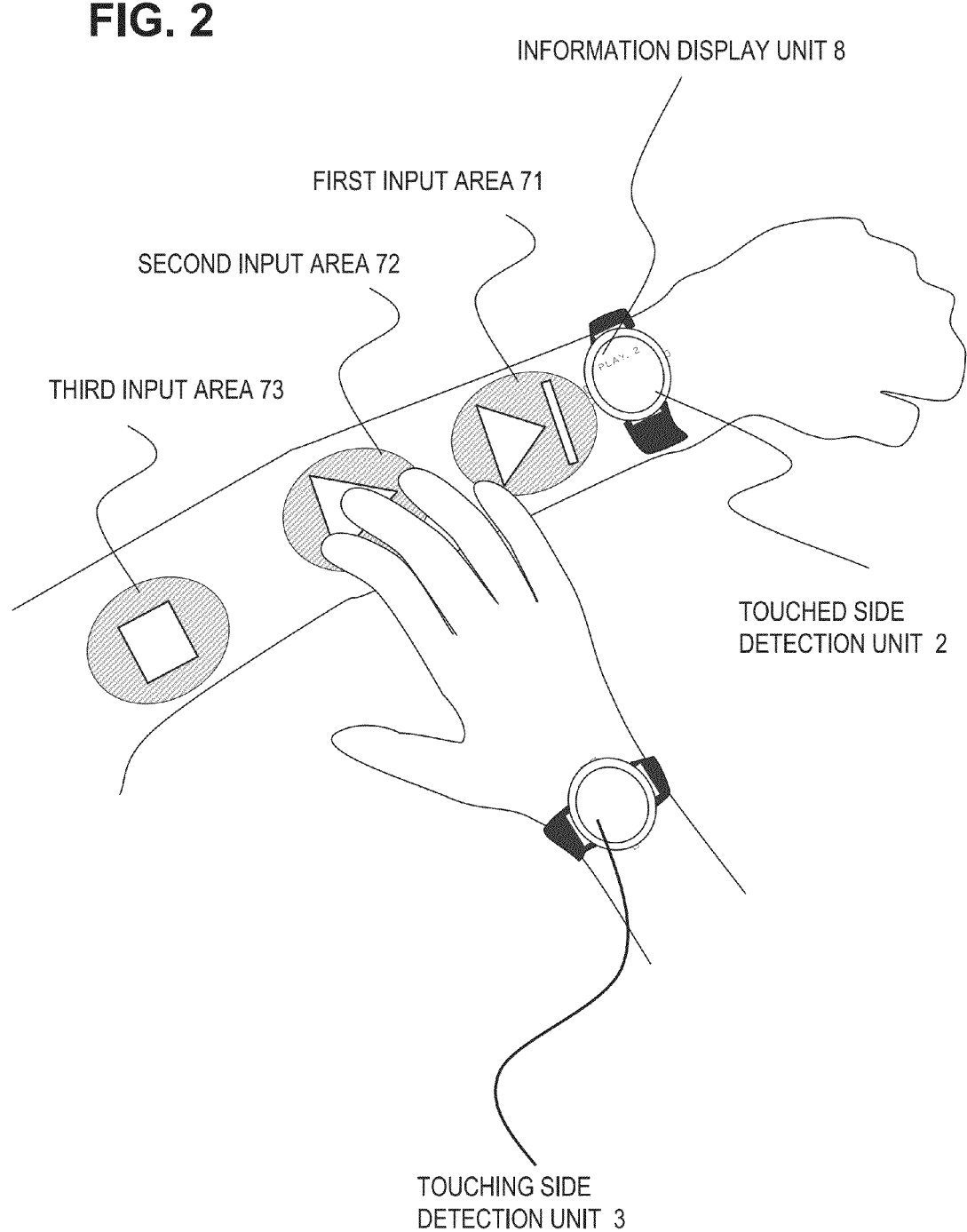
FIG. 2 is a drawing showing a detailed configuration of input areas for the input device relating to the first exemplary embodiment.

FIG. 2 is a drawing showing details of input areas when an operated device is a portable music player and an arm of a user is used as an input unit. In FIG. 2, three input areas 71 to 73 for operating the device are provided on the arm. In the present exemplary embodiment, a music operation is imagined as an example. "Skip Forward" function, "Play/Pause" function, and "Stop" function are assigned to the input areas 71 to 73 provided on the wrist side of the forearm, the upper arm of the forearm, and the upper arm, respectively.

The user performs an input operation by tapping the input areas 71 to 73 on an arm using the other arm. For instance, when the user is jogging or walking while listening to music, he or she is able to perform an operation corresponding to the tap position by tapping the arm, avoiding the trouble of taking out the portable music player and operating small input keys.

FIG. 1 is a block diagram showing a configuration of the input device relating to the present exemplary embodiment.

In FIG. 1, the input device comprises a detection unit 1, a storage unit 4, an input information identification unit 5, and an information display unit 6.

The detection unit 1 includes two detection units, i.e., a touching side detection unit 3 (first detection unit) and a touched side detection unit 2 (second detection unit). Upon detecting a vibration that is generated by tapping on the body of the user and transmitted through the body of the user, the touched side detection unit 2 on the tapped side outputs touched side detection data "a" and the touching side detection unit 3 on the tapping side outputs touching side detection data "b."

The storage unit 4 holds an association between the time difference between vibrations detected by the touched side detection unit 2 and the touching side detection unit 3 and a tap position as determination data "c" in advance.

The input information identification unit 5 receives the touched side detection data "a" and touching side detection data "b," calculates the time difference between them, identifies a tap position by referring to the determination data "c" stored in the storage unit 4, and outputs a command assigned to the tap position as input information identification data "d."

Upon receiving the input information identification data "d," the information display unit 6 performs an operation corresponding to the command, such as playing/pausing music, and outputs a screen display attached thereto.

In FIG. 2, the touched side detection unit 2 for detecting a vibration is provided on the wrist of the left arm that is being tapped. Meanwhile, the touching side detection unit 3 for detecting a vibration is provided on the wrist of the right arm, which does the tapping.

Figure 3:
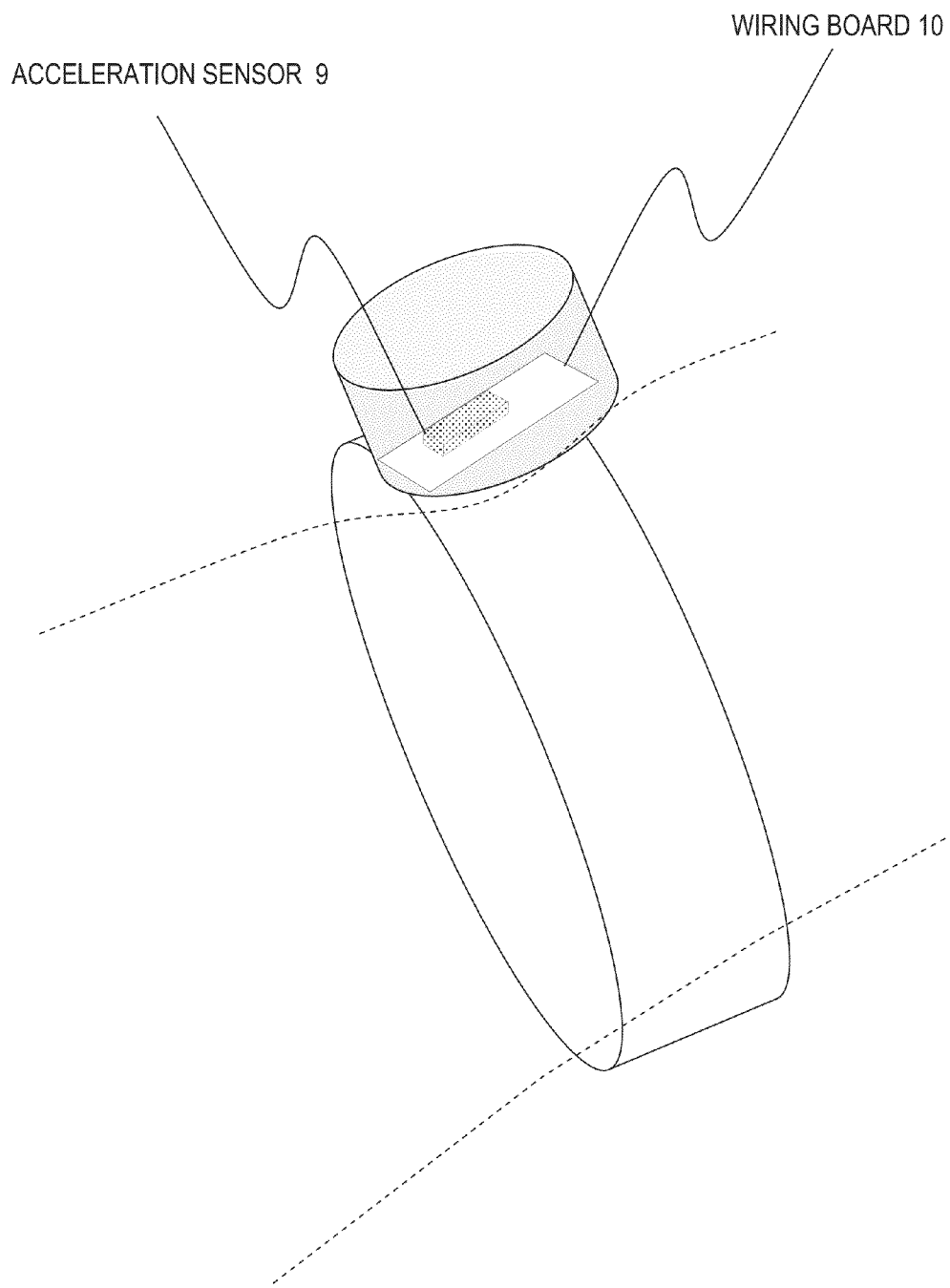
FIG. 3 is a drawing showing a detailed configuration of a detection unit of the input device relating to the first exemplary embodiment.

FIG. 3 is a drawing showing a detailed configuration of the detection unit 1. In FIG. 3, each of the touched side detection unit 2 and the touching side detection unit 3 included in the detection unit 1 has an acceleration sensor 9 provided on a wiring board 10 and detects a vibration as acceleration using the acceleration sensor 9.

Figure 4:
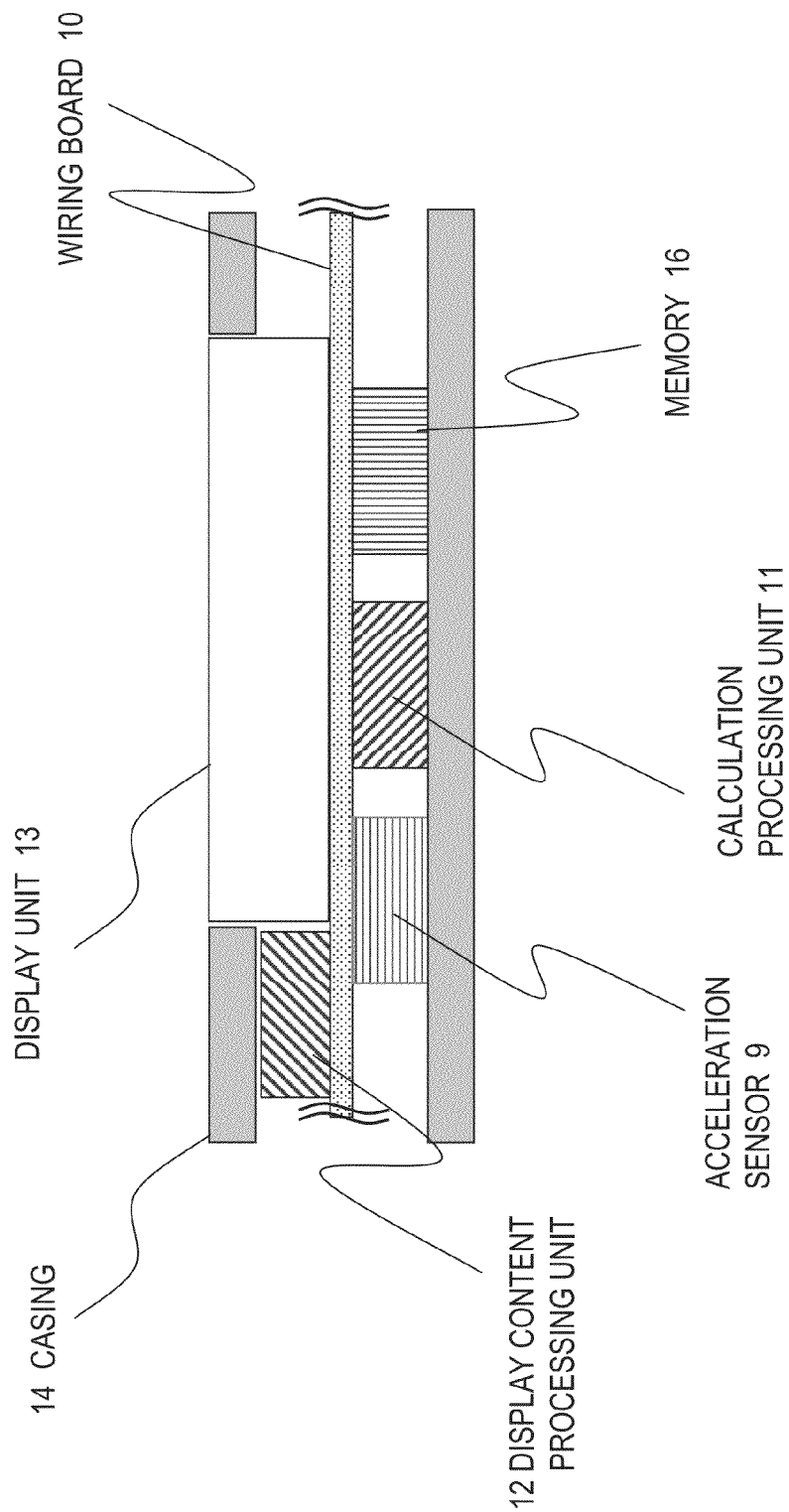
FIG. 4 is a cross-sectional view showing a detailed configuration of the detection unit of the input device relating to the first exemplary embodiment.

FIG. 4 is a cross-sectional view showing a detailed configuration of the detection unit 1. In FIG. 4, a memory 16, a calculation processing unit 11, a display content processing unit 12, and a display unit 13 are provided on the wiring board 10, in addition to the acceleration sensor 9. Further, each unit is cased in a casing 14. The memory 16 holds the determination data "c" of the storage unit 4. The calculation processing unit 11 performs the processing in the input information identification unit 5. The display content processing unit 12 controls play/pause of music and a texture on the screen outputted by commands assigned to tap positions in the information display unit 6. The display unit 13 outputs an audio signal controlled by the display content processing unit 12 through a speaker, and transmits data to another display device such as a Bluetooth (registered trademark) device, or outputs a controlled pixel signal to a display.

Figure 5:
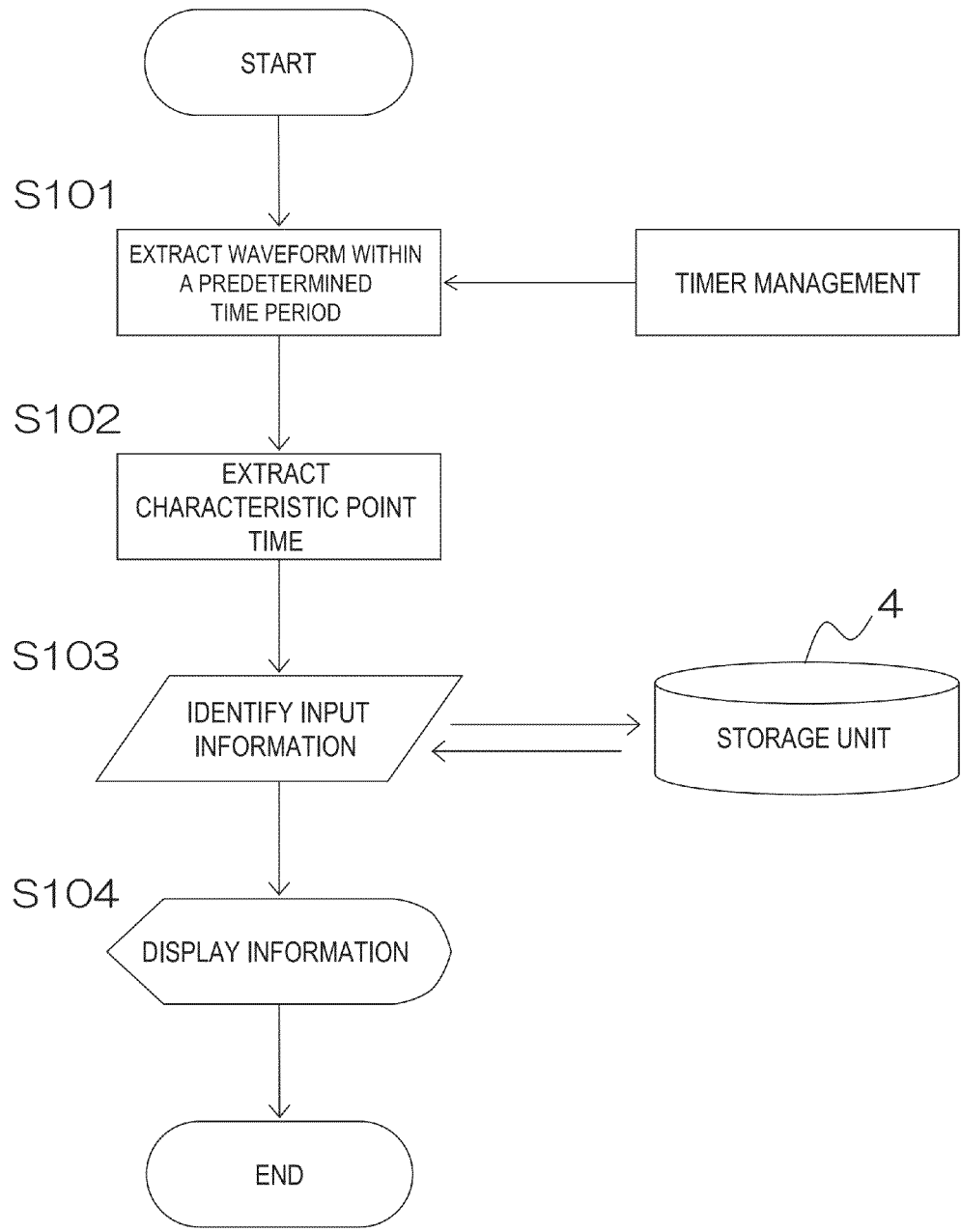
FIG. 5 is a flowchart showing an operation of the input device relating to the first exemplary embodiment.

Next, an operation of the entire input device relating to the present exemplary embodiment will be described with reference to the drawings. FIG. 5 is a flowchart showing the operation of the input device of the present exemplary embodiment.

First, when one hand taps the input areas 71 to 73 on the other arm, the touched side detection unit 2 and the touching side detection unit 3 extract data within a predetermined period of time from the touched side detection data "a" and the touching side detection data "b" showing vibration waveforms, which are the time-series data of values detected by the acceleration sensor 9 for each sampling period (step S101). For instance, each of the touched side detection unit 2 and the touching side detection unit 3 extracts a vibration waveform within a predetermined period of time from the time when the input operation is detected from the touched side detection data "a" and the touching side detection data "b" as data for identifying the touched position.

The time required for each vibration caused by an input tap operation to be transmitted varies due to a difference in the vibration transmission path from the tap position to each detection unit. Therefore, the touching side detection unit 3 and the touched side detection unit 2 extracts a characteristic point time for deriving the time when a vibration arrives based on the touched side detection data "a" and the touching side detection data "b," and outputs it to the input information identification unit 5 (step S102).

Next, the input information identification unit 5 refers to the determination data "c" of the storage unit 4 that holds the association between the time difference caused by the difference in the vibration transmission path from the tap position to each detection unit and the tap position, and associates the time difference with the tap position. As a result, the input information identification unit 5 identifies which input area has been tapped and outputs the result as the input information identification data "d" (step S103).

Finally, the information display unit 6 displays a predetermined symbol, data, and function assigned to the identified input area (step S104).

Next, the operation of each step will be described in detail.

FIGS. 6A, 6B, and 6C are drawings for explaining the vibration waveform extraction in the step S101. When receiving vibration waveforms, which are the time-series data of values detected by the touched side detection unit 2 and the touching side detection unit 3, as the touched side detection data "a" and the touching side detection data "b," respectively, the input information identification unit 5 extracts data within a predetermined period of time from the time when the input operation is performed from each detected data, as comparison data. Detected vibrations are a vibration waveform, shown in FIG. 6A, in the touching side detection unit 3, and a vibration waveform, shown in FIG. 6B, in the touched side detection unit 2. Note that it is preferable that the input information identification unit 5 receive detected data for each predetermined time interval in bulk since communication will require so much time when values of detected data at each time period are sequentially processed.

Figure 7A:
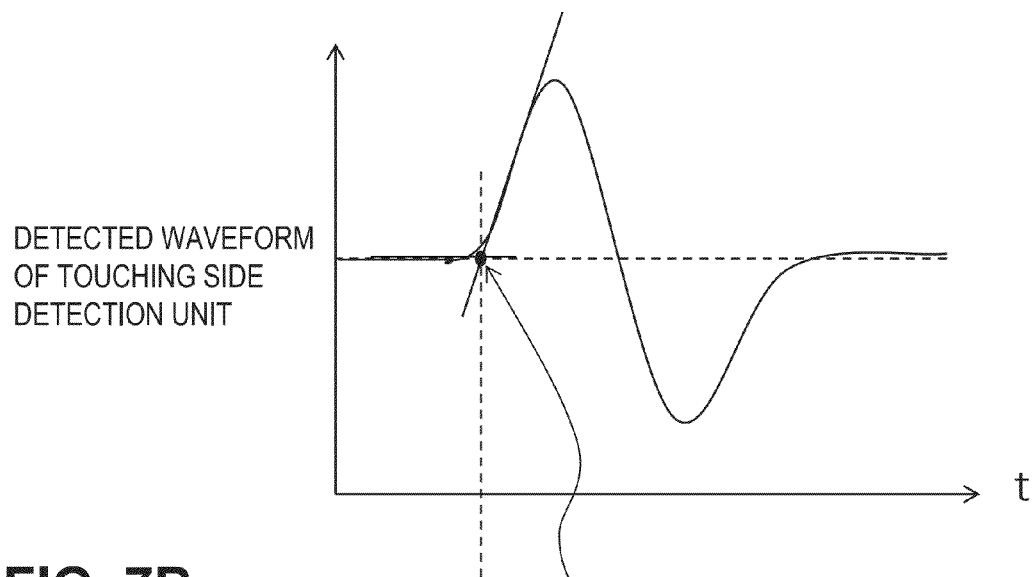
FIGS. 7A and 7B are drawings for explaining vibration arriving time extraction performed by the input device relating to the first exemplary embodiment.
Figure 7B:
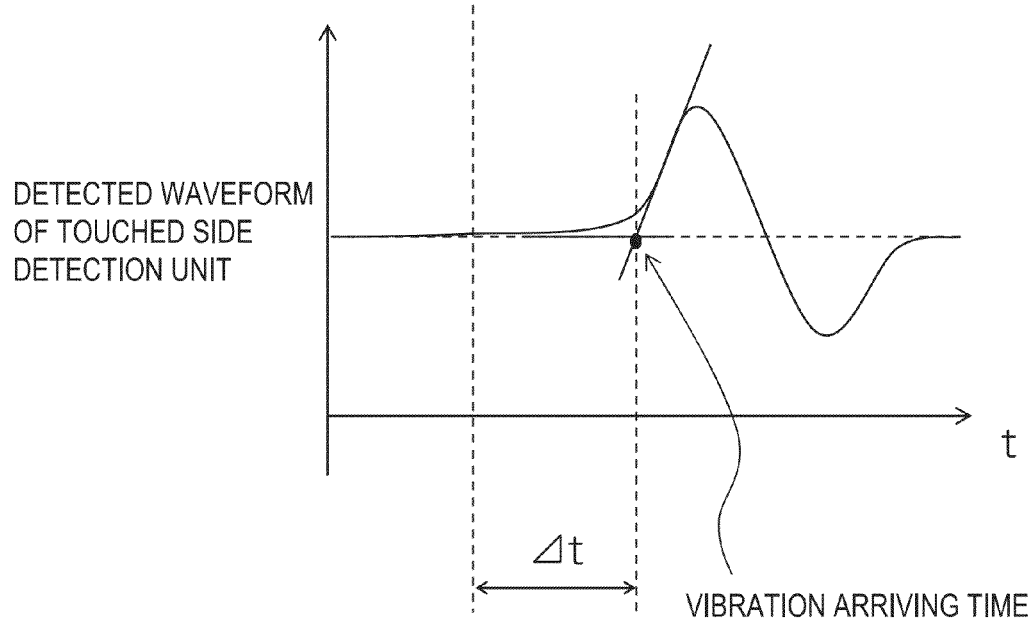

FIGS. 7A and 7B are drawings for explaining the vibration arriving time extraction in the step S102. The touched side detection unit 2 and the touching side detection unit 3 extract the rise time of the vibration waveforms in order to calculate the time when the vibration caused by an input tap operation was detected. With reference to FIGS. 7A and 7B, as an example, the time of the intersection between a tangent of data in which the vibration has not arrived and the waveform is stable and a tangent of the place where the slope is maximum at the rise of the waveform may be calculated as the vibration arriving time.

Here, a method using the time difference to associate the difference in the length of the vibration transmission path from the tap position to each detection unit with the tap position will be described.

Figure 8:
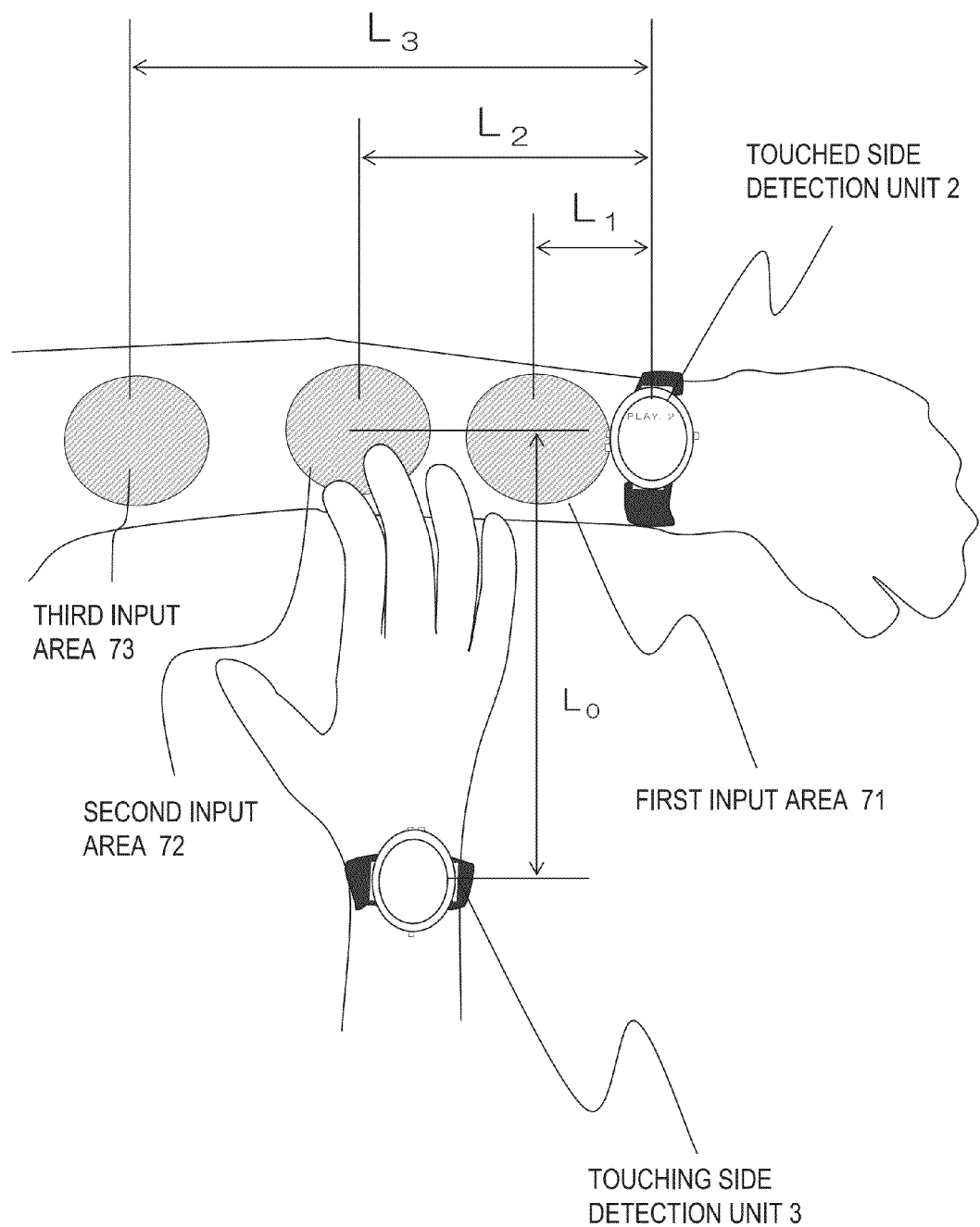
FIG. 8 is a drawing showing a transmission path length from each detection unit to each input area of the input device relating to the first exemplary embodiment.

FIG. 8 is a drawing showing the transmission path length from each detection unit to each input area. The tapped arm is divided into three regions of the wrist side of the forearm, the upper arm side of the forearm, and the upper arm, and the first input area 71, the second input area 72, and the third input area 72 are provided on the three regions, respectively. Note that the input areas 71 to 73 are regions for the sake of convenience of explanation and no device for detecting a position is provided on the arm. Further, the distances from the touched side detection unit 2 to the centers of the input areas 71 to 73 are referred to as $L_1$ to $L_3$, respectively, and the distance from the touching side detection unit 3 to the tap position is referred to as $L_0$.

FIG. 9 is a table showing the vibration transmission time and detection time difference in each detection unit. It is assumed that a tapping input operation on the input areas 71 to 73 is performed by touching the center of each input area.

In a case where an input operation is performed on the first input area 71, when the distance from the tap position to the touched side detection unit 2 is $L_1$ and the vibration transmission speed is v, it takes time of $L_1/v$ to detect the vibration from the point in time when the tap operation is performed. Further, the distance from the tap position to the touching side detection unit 3 is $L_0$, and it takes time of $L_0/v$ to detect the vibration from the point in time when the tap operation is performed. Therefore, the detection time difference is $(L_1-L_0)/v$ in this case.

Similarly, in a case of input on the second input area 72, the detection time difference is $(L_2-L_0)/v$. Further, in a case of input on the third input area 73, the detection time difference is $(L_3-L_0)/v$. Since the distance $L_0$ from the tap position to the touching side detection unit 3 is constant, the detection time difference between the touching side detection unit 3 and the touched side detection unit 2 can be associated with the distance from the tap position to the touched side detection unit 2, i.e., any one of the distances $L_1$ to $L_3$.

Figure 10:
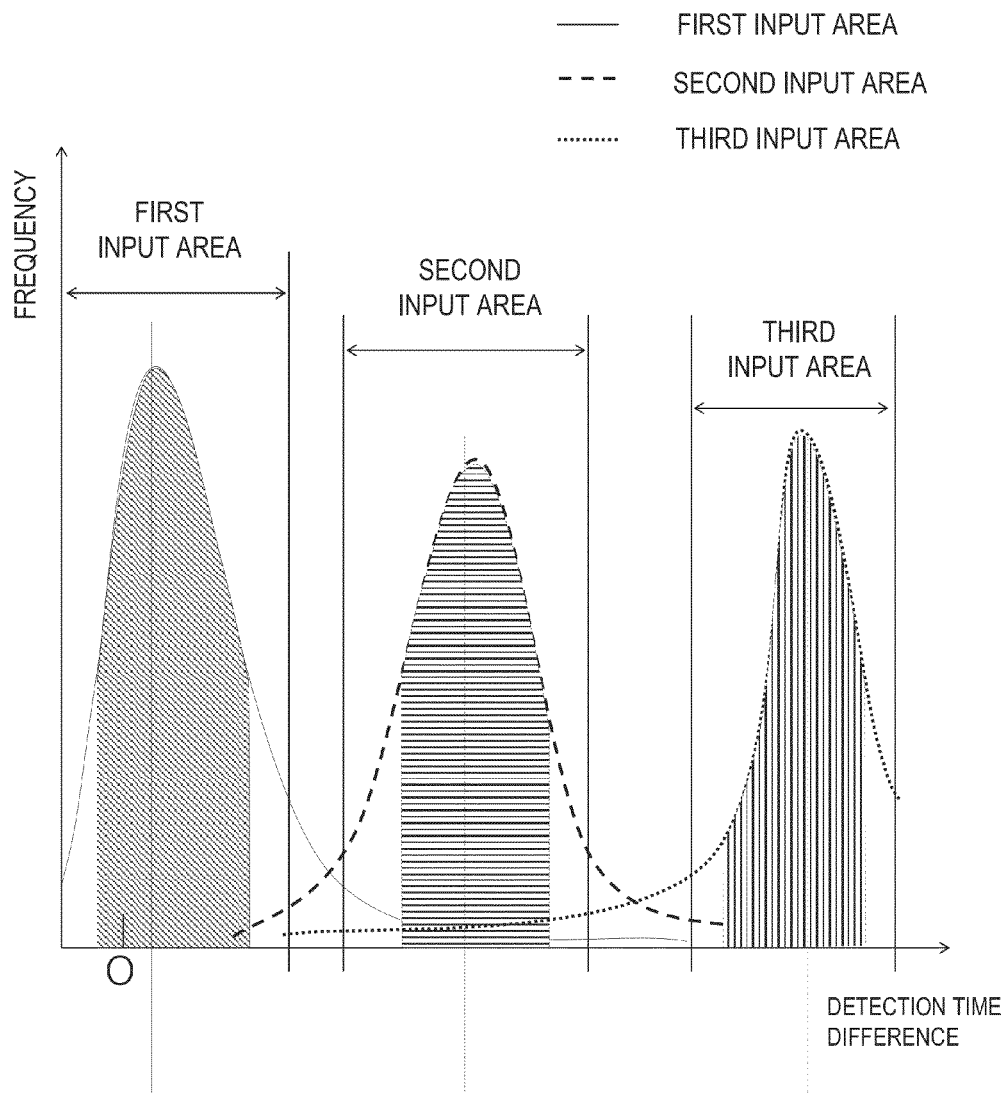
FIG. 10 is a drawing showing a detection time difference of each input area of the input device relating to the first exemplary embodiment and the frequency distribution thereof.

FIG. 10 is a drawing showing the detection time difference of each input area and the frequency distribution thereof. With reference to FIG. 10, an operation of the input information identification unit 5 to identify the input information (the step S103) will be described. Variation in input tapping position for each of the input areas 71 to 73 follows a normal distribution. Therefore, upper and lower threshold values may be provided, and the input information identification unit 5 may recognize values included in the range between these thresholds as input on each input area.

The vibration transmission speed varies for each user due to individual differences. Further, even for the same user, the tap position on each of the input areas 71 to 73 varies. Moreover, there is variation caused by the way the body contacts the device. Therefore, a range for recognizing input on each input area is set with a standard deviation a as a reference so that the ranges do not overlap each other. For instance, the range may be set with a lower threshold of $\mu-2\sigma$ and an upper threshold of $\mu+2\sigma$ using the average $\mu$ as the center. In this case, 95.45 percent of all data is included in the range of $\mu\pm\sigma$.

It is preferred that the threshold values for the input information identification by the detection time difference between the touching side detection unit 3 and the touched side detection unit 2 be stored in advance as the determination data "c" of the storage unit 4.

FIG. 11 is a table showing an association between the lower and upper thresholds included in the determination data "c" stored in the storage unit 4 and the input information identification data "d" as an example. In order to store only the lower and upper thresholds as the determination data "c" of the storage unit 4, a plurality of detection time differences when each of the input areas 71 to 73 is tapped are obtained at the time of creating the data of the storage unit 4, the lower and upper thresholds are derived by subtracting/adding the standard deviation from/to the average of the normal distribution, respectively, and the determination data "c" is created by associating these thresholds with the input areas 71 to 73.

For instance, when the detection time difference between the touching side detection unit 3 and the touched side detection unit 2 is 0.005 [s], with reference to FIG. 11, this detection time difference is between the lower and upper thresholds for the third input area 73. Therefore, a command assigned to the third input area 73 (i.e., "Stop") is selected.

Note that the input information identification unit 5 may hold the thresholds and refer thereto when identifying the input information, instead of having the thresholds included in the determination data "c" of the storage unit 4.

Next, an operation of the information display unit 6 (the step S104) will be described.

Upon receiving the input information identification data "d" identified by the input information identification unit 5, the information display unit 6 displays the function assigned to the input position to the user. Since a music operation is assumed in the present exemplary embodiment, music data is controlled and sound is outputted from the speakers according to the function assigned to each of the input area 71 to 73, i.e., "Skip Forward," "Play/Pause," and "Stop."

Further, the information display unit 6 may transmit data to earphones or headphones via Bluetooth or display the title of a song being played back or the function being executed on the display according to the function assigned to each of the input area 71 to 73.

The rise time of the vibration waveform is extracted as the vibration arriving time in the present exemplary embodiment, however, a time constant may be provided to extract time when a stable vibration is deemed to be transmitted and time when this value is exceeded may be deemed to be the vibration transmission time. Further, an extreme value of the vibration waveform may be deemed to be the vibration transmission time as time when a main vibration has been transmitted. Moreover, since the shapes of vibration waveforms generated by tap operations are similar to each other, a vibration waveform may be generated as a template and the vibration transmission time may be calculated based on template matching.

Further, in the present exemplary embodiment, the three input areas 71 to 73 are provided on the arm and a command is assigned to each input area. The number of the input areas and the command assigned thereto, however, may be set as necessary without being limited to the aspect of the present exemplary embodiment.

Further, in the present exemplary embodiment, all the input areas 71 to 73 are assigned to an arm. The input areas, however, may be set on a place other than an arm as long as it is within the transmission range of vibrations.

Further, in the present exemplary embodiment, the touched side detection unit 2 is provided on the left hand and the touching side detection unit 3 is provided on the right hand. This placement, however, can be obviously reversed. Further, the attachment location of these detection units is not limited to a wrist. In other words, the detection units may be attached to a forearm, glove, ring, and an ankle as long as it is within the transmission range of vibrations.

(Second Exemplary Embodiment)

An input device relating to a second exemplary embodiment will be described with reference to the drawings.

In the first exemplary embodiment, the difference in the vibration transmission path from the tap position to each of the two detection units is calculated as the difference in the time required for the transmission, and the input area is identified by associating the time difference between the detection units with the tap position. Meanwhile, in the present exemplary embodiment, the input area is identified by detecting the difference in the vibration transmission path from the tap position to each detection unit as a difference in the strength of the vibration transmission.

Figure 12:
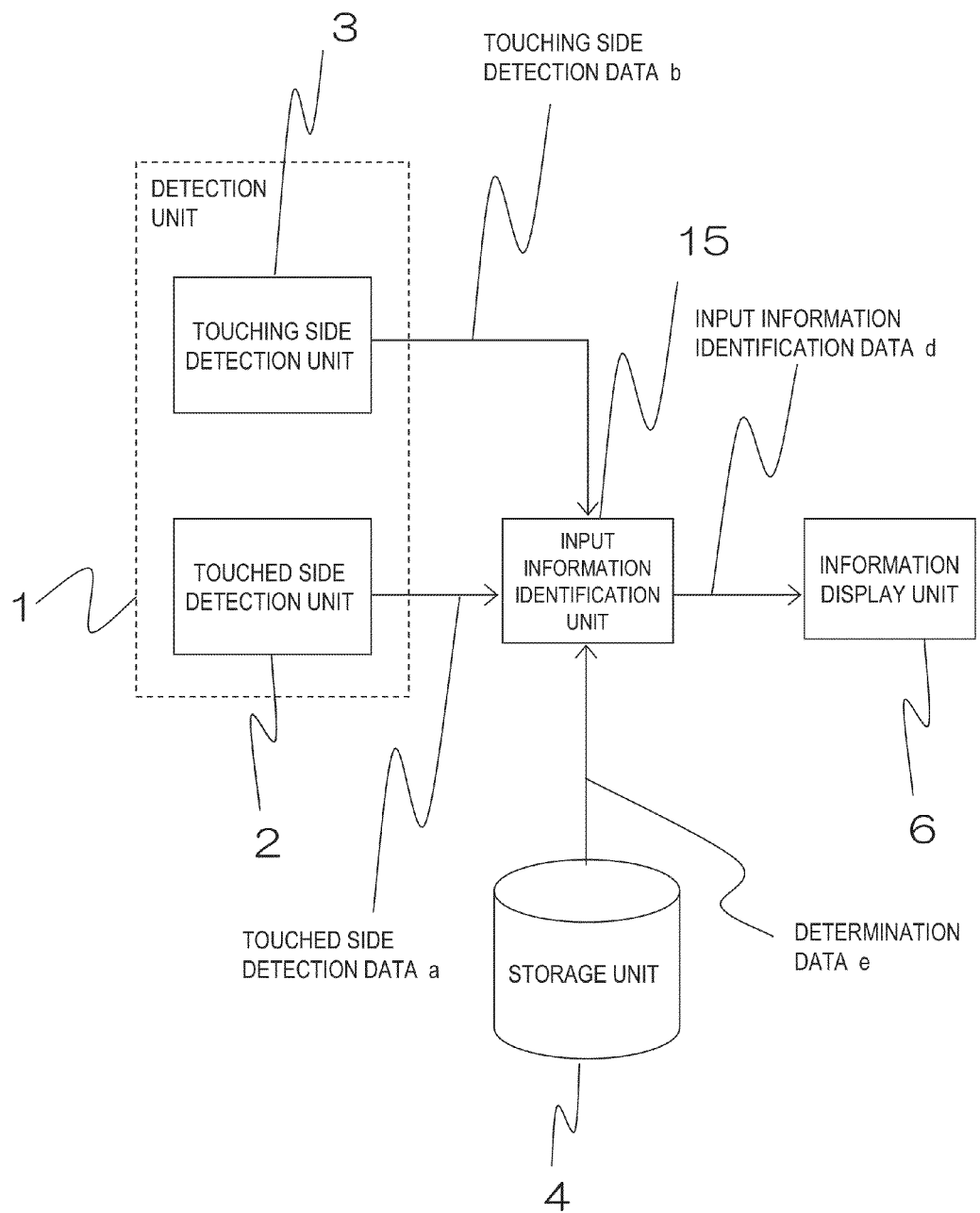
FIG. 12 is a block diagram showing a configuration of an input device relating to a second exemplary embodiment.

FIG. 12 is a block diagram showing a configuration of the input device of the present exemplary embodiment. In the first exemplary embodiment, the association between the time difference between vibrations detected by the touched side detection unit 2 and the touching side detection unit 3, and the tap position is stored in the storage unit 4 in advance as the determination data "c" in order to identify the tap position. Meanwhile, in the present exemplary embodiment, an association between the ratio of vibration strength detected by the touched side detection unit 2 and the touching side detection unit 3, and the tap position is stored in the storage unit 4 in advance as determination data "e."

Further, the input device of the present exemplary embodiment comprises an input information identification unit 15, instead of the input information identification unit 5 in the input device of the first exemplary embodiment. Upon receiving the touched side detection data "a" and the touching side detection data "b," the input information identification unit 15 identifies the tap position by referring to the determination data "e" of the storage unit 4 and extracting the ratio of the vibration strength detected by the touched side detection unit 2 and the touching side detection unit 3.

In the first exemplary embodiment, the input information identification unit 5 identifies the tap position using the time difference between vibrations detected by the touched side detection unit 2 and the touching side detection unit 3. Meanwhile, in the present exemplary embodiment, the tap position is identified using the ratio of the vibration strength detected by the touched side detection unit 2 and the touching side detection unit 3. This is due to the fact that the degrees of attenuation of vibrations are different because of the difference in the vibration transmission path from the tap position to each detection unit and the strength of the vibration detected by each detection unit is different.

First, an operation of input information identification unit 15 will be described in detail.

Figure 13:
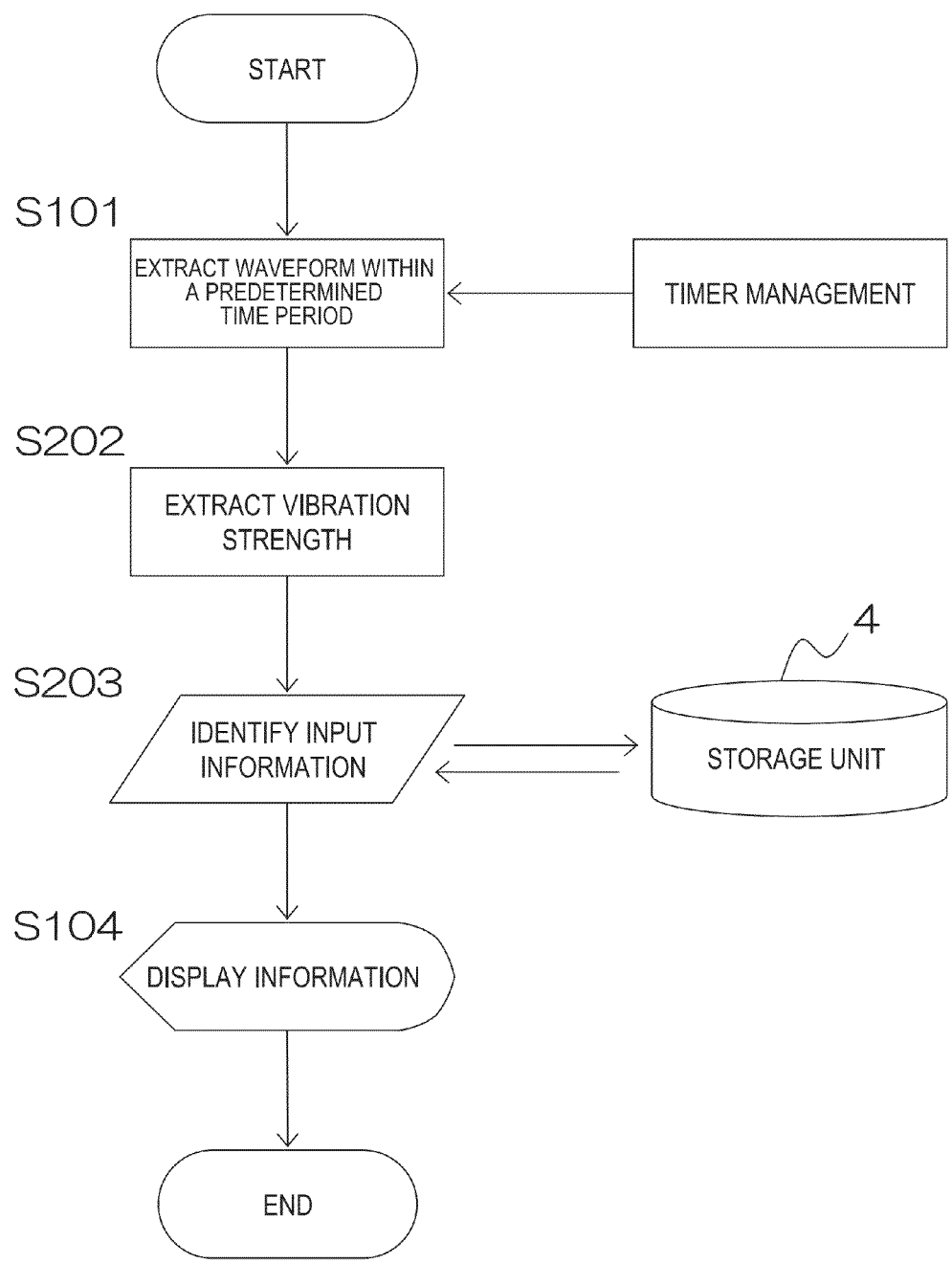
FIG. 13 is a flowchart showing an operation of the input device relating to the second exemplary embodiment.

FIG. 13 is a flowchart showing the operation of the input device relating to the present exemplary embodiment. The input device of the first exemplary embodiment extracts the characteristic point time in the step S102 of FIG. 5. Meanwhile, the input device of the present exemplary embodiment extracts the vibration strength detected by the touched side detection unit 2 and the touching side detection unit 3 based on the touched side detection data "a" and the touching side detection data "b" (step S202).

Figure 14A:
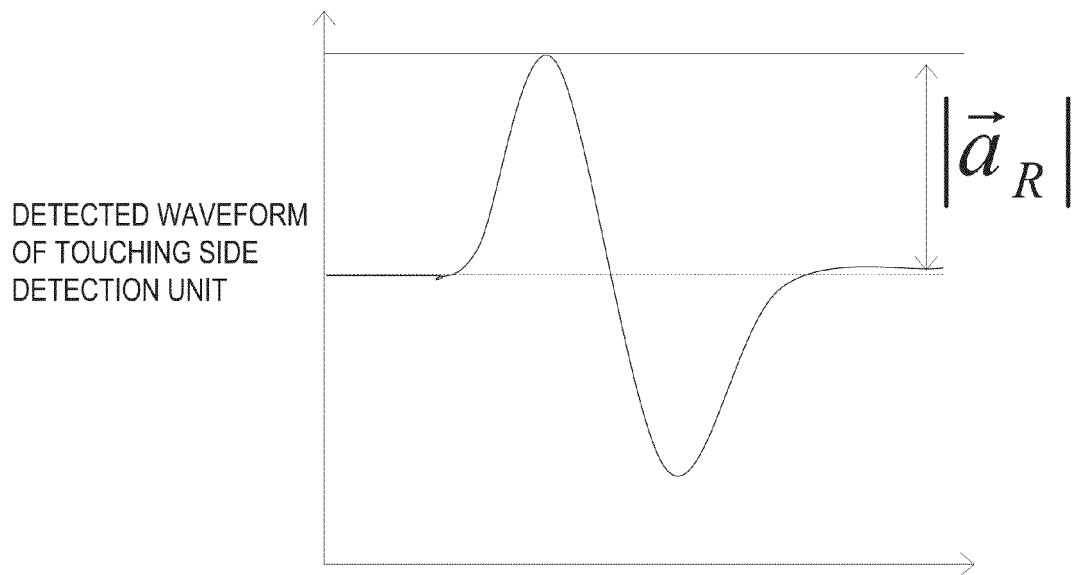
FIGS. 14A and 14B are drawings showing the vibration strength in each detection unit of the input device relating to the second exemplary embodiment as an example.
Figure 14B:
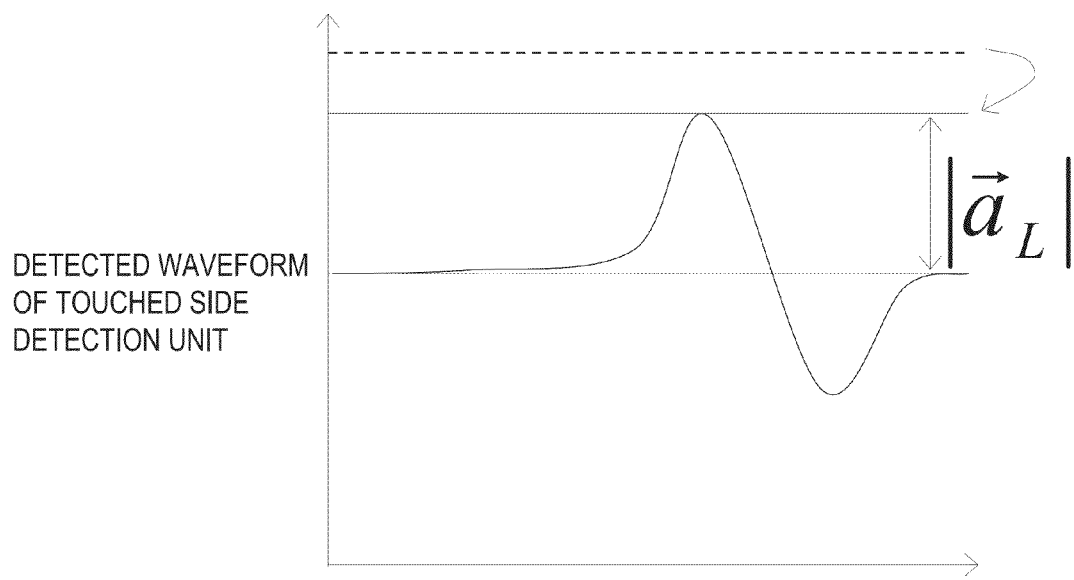

FIGS. 14A and 14B are drawings showing the vibration strength in the detection units as examples. In the step S202, for instance, extreme values of the amplitude are extracted as an indicator of the vibration strength detected by the touched side detection unit 2 and the touching side detection unit 3.

In the first exemplary embodiment, which input area has been tapped is identified in the step S103 of FIG. 5 by referring to the determination data "c" of the storage unit 4 that holds the association between the time difference of vibrations detected by the two detection units and the tap position. Meanwhile, in the present exemplary embodiment, the input information identification unit 15 identifies which of the input areas 71 to 73 has been tapped by referring to the determination data "e" of the storage unit 4 that holds the association between the ratio of the vibration amplitude detected by the two detection units and the tap position and by associating the amplitude ratio and the tap position (step S203).

Next, an operation of the input information identification unit 15 in the step S203 will be described in detail.

FIG. 15 is a table showing an association between lower and upper thresholds and the input information identification data "d." First, the ratio of the maximum value of the vibration amplitude at each detection unit $R=|aL|/|aR|$ is calculated where $|aR|$ is the vibration impact at the touching side detection unit 3 and $|aL|$ is the vibration impact at the touched side detection unit 2. Values stored in the storage unit 4 as the determination data "e" are created based on R, the ratio of the maximum value of the vibration amplitude at each detection unit.

When a tap operation is performed on the input areas 71 to 73, the input information identification unit 15 identifies the tap position based on whether or not the value is within a range between the lower and upper thresholds of the ratio R, the determination data "e." Note that the lower and upper thresholds of the ratio R may be μ−2σ and μ+2σ, respectively, where μ is the average and σ is the standard deviation.

In the present exemplary embodiment, the maximum value of the amplitude is used as an indicator of the strength of the vibration transmitted. Note that the vibration energy obtained by integrating the vibration waveform may be used as an indicator of the vibration strength.

Further, the lower and upper thresholds of the determination data "e" are μ−2σ and μ+2σ, respectively, however, the lower and upper thresholds are not limited to these values.

(Third Exemplary Embodiment)

An input device relating to a third exemplary embodiment will be described with reference to the drawings.

In the second exemplary embodiment, in which of the input areas 71 to 73 the tap position is included is identified by comparing the ratios of the vibration amplitude detected by the two detection units. Meanwhile, in the present exemplary embodiment, one identifies the input area on which a tap operation is performed using only the impact at the touched side detection unit 2.

Figure 16:
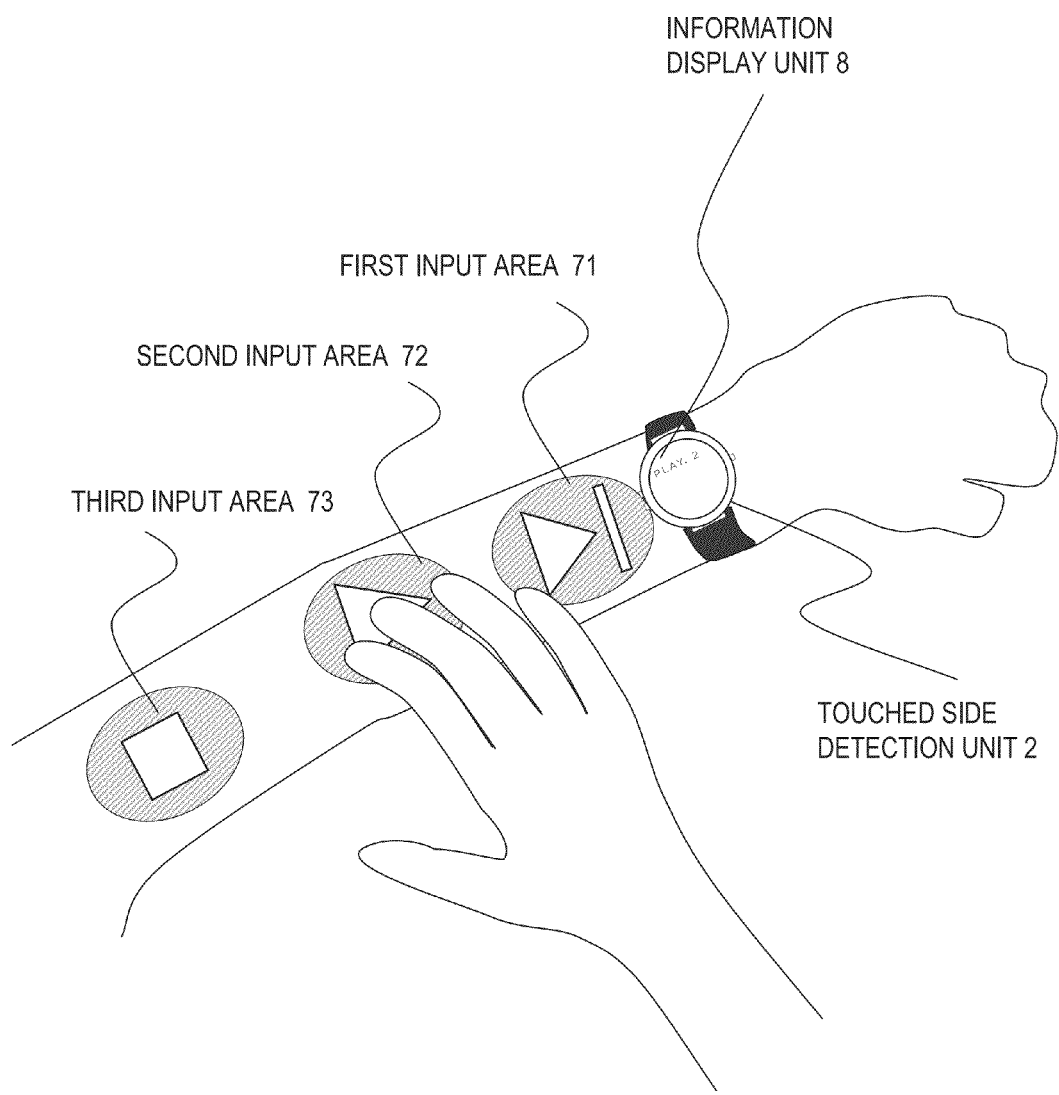
FIG. 16 is a drawing showing input areas and a detection unit in an input device relating to a third exemplary embodiment.

FIG. 16 is a drawing showing the input areas 71 to 73 and the detection unit 1. With reference to FIG. 16, the detection unit 1 comprises only the touched side detection unit 2 in the present exemplary embodiment, unlike the second exemplary embodiment.

Figure 17:
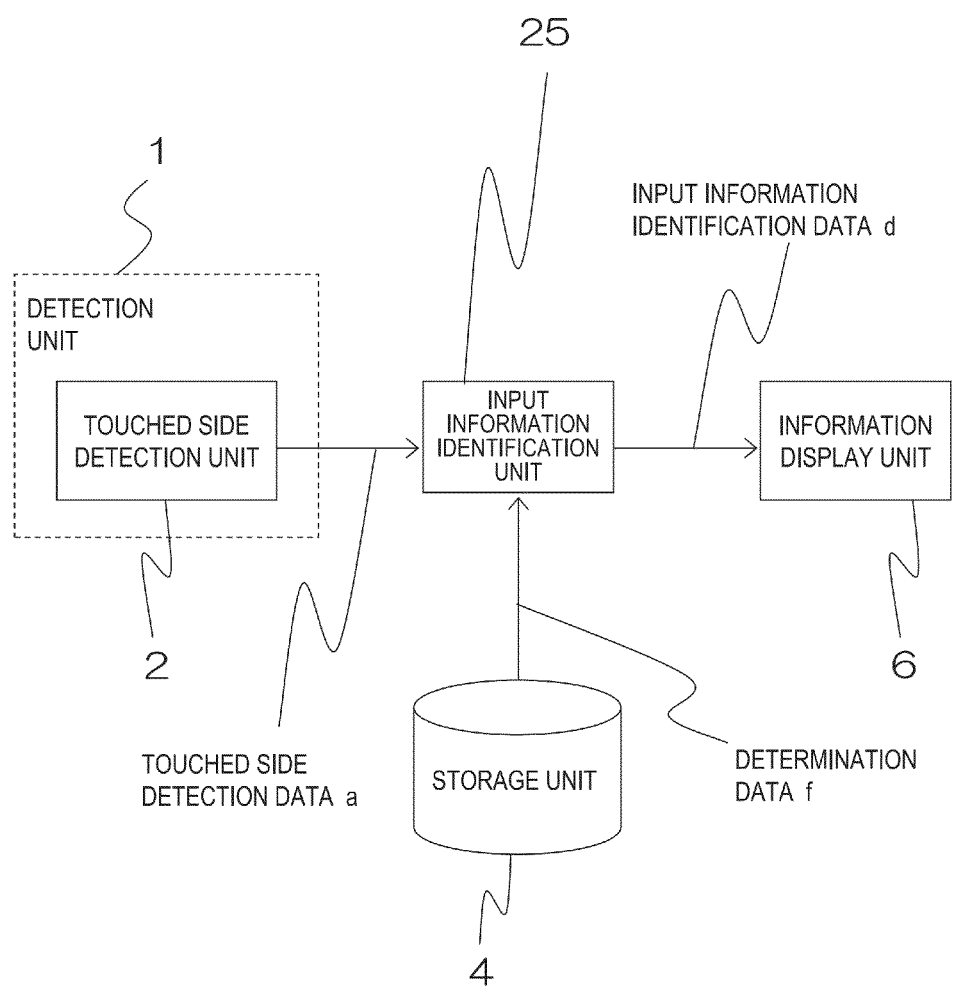
FIG. 17 is a block diagram showing a configuration of the input device relating to the third exemplary embodiment.

FIG. 17 is a block diagram showing a configuration of the input device relating to the present exemplary embodiment. In the second exemplary embodiment shown in FIG. 12, the detection unit 1 includes two detection units: the touched side detection unit 2 and the touching side detection unit 3. With reference to FIG. 17, the detection unit 1 includes only the touched side detection unit 2 on the tapped side in the present exemplary embodiment.

In the second exemplary embodiment, the association between the ratio of the vibration impact at each detection unit and the tap position is stored in the storage unit 4 as the determination data "e" in advance. Meanwhile, in the present exemplary embodiment, an association between the strength of vibrations detected by the touched side detection unit 2 and the tap position is stored in the storage unit 4 as determination data "f" in advance.

Further, in the second exemplary embodiment, the input information identification unit 15 identifies the tap position by referring to the determination data "e" and calculating the ratio of the vibration amplitude detected by the touched side detection unit 2 and the touching side detection unit 3. Meanwhile, in the present exemplary embodiment, upon receiving the touched side detection data "a," an input information identification unit 25 identifies the tap position by referring to the determination data "f" of the storage unit and to the strength of vibrations detected by the touched side detection unit 2.

In the input device of the second exemplary embodiment, when the strength of tap operations by the user is almost constant, the touching side detection data "b" becomes nearly constant as well. Therefore, the tap position can be identified based on only the strength of vibrations detected by the touched side detection unit 2. According to the input device of the present exemplary embodiment, the user does not need to wear detection units on both touching and touched sides, unlike the input device of the second exemplary embodiment.

(Fourth Exemplary Embodiment)

An input device relating to a fourth exemplary embodiment will be described with reference to the drawings.

In the first to the third exemplary embodiments, there are three input areas 71 to 73 for operating the device on the arm, and the input area is identified using the detection data depending on the length of the vibration transmission path from the tap position. Meanwhile, in the present exemplary embodiment, different input areas are identified according to the posture of the tapped arm based on touched side detection data "p" of the touched side detection unit 2, in addition to the length of the vibration transmission path from the tap position.

Figure 18:
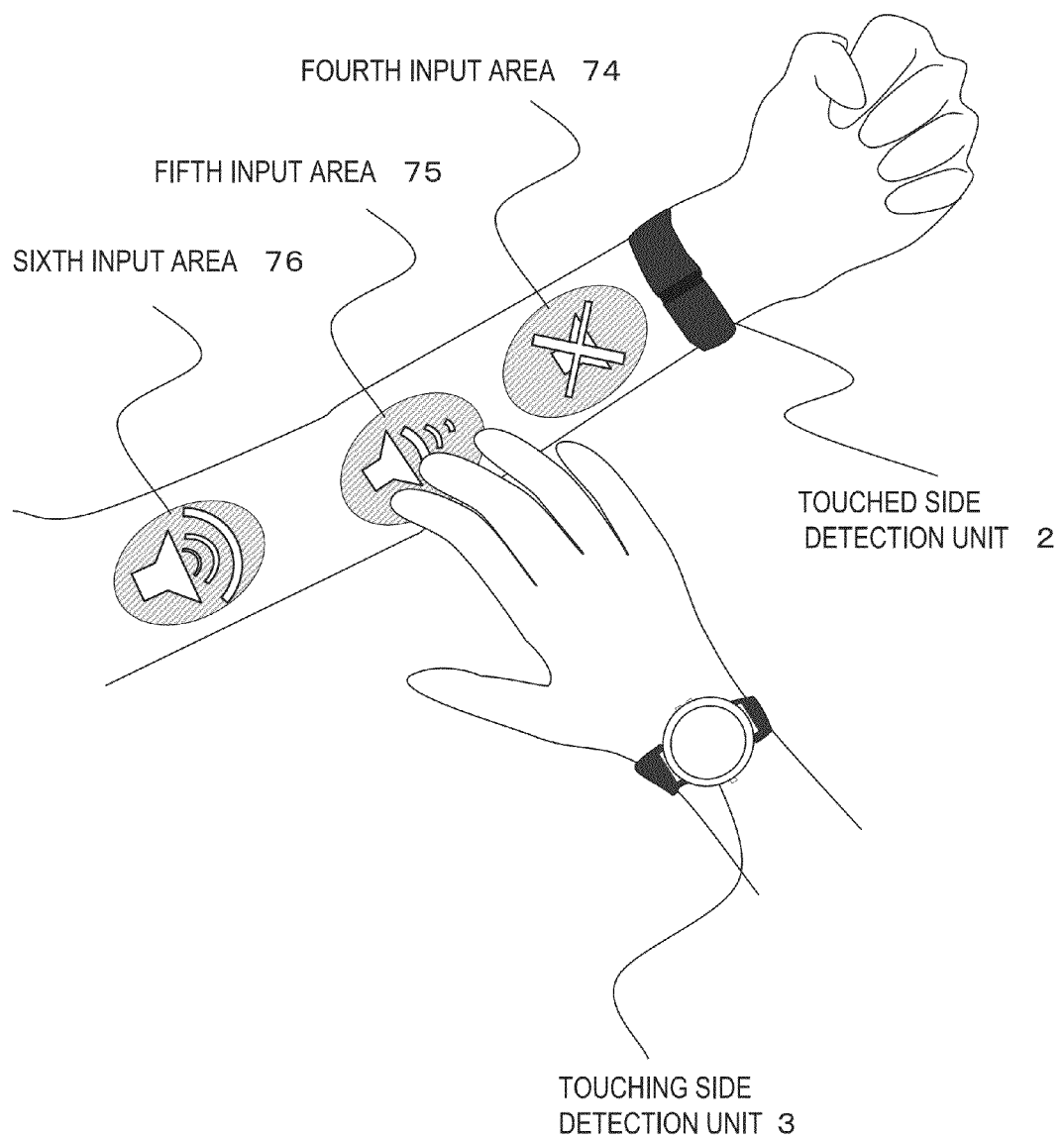
FIG. 18 is a drawing showing input areas and detection units in an input device relating to a fourth exemplary embodiment.

FIG. 18 is a drawing showing each input area on the palm side of the arm. The posture of the tapped arm is different from FIG. 2; the palm side of the arm is facing upward, and a fourth input area 74, a fifth input area 75, and a sixth input area 76 are provided in three regions of the wrist side of the forearm, the upper arm side of the forearm, and the upper arm, respectively.

Figure 19:
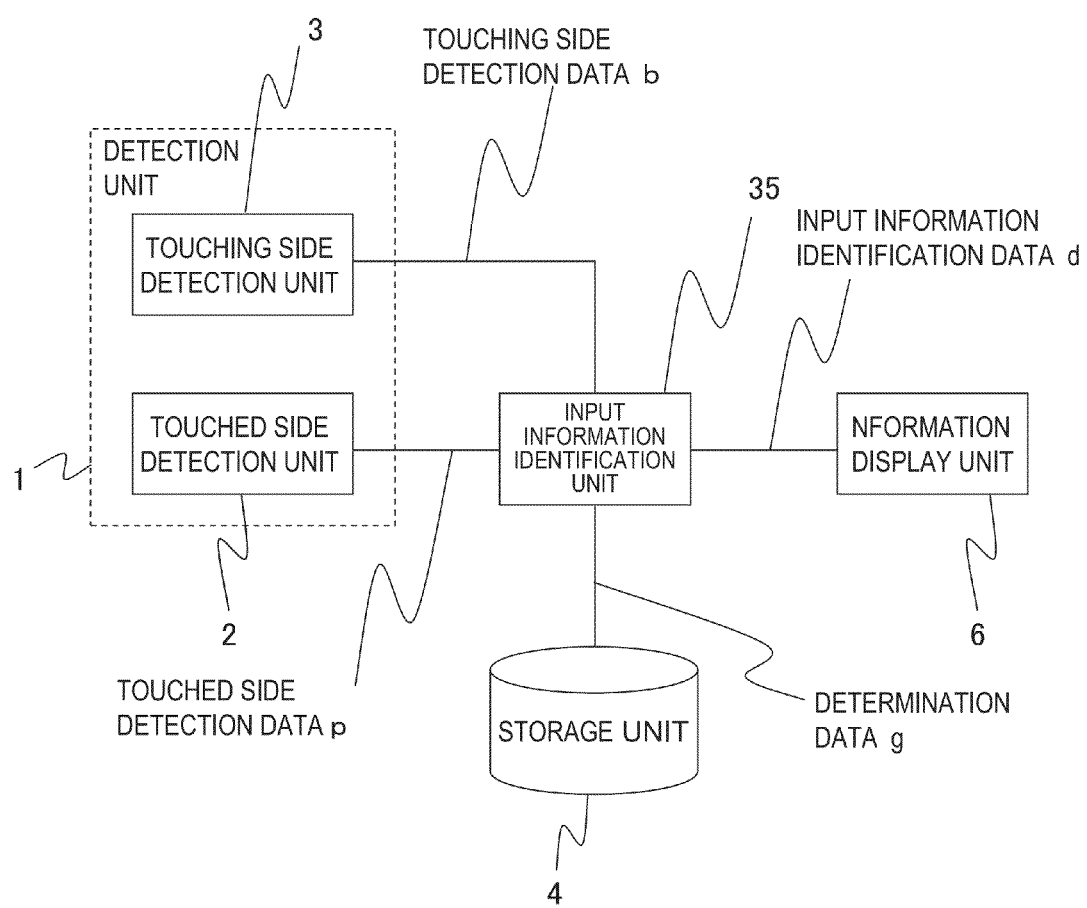
FIG. 19 is a block diagram showing a configuration of the input device relating to the fourth exemplary embodiment.

FIG. 19 is a block diagram showing the configuration of the input device of the present exemplary embodiment. In the first exemplary embodiment, the association between the time difference between vibrations detected by the touched side detection unit 2 and the touching side detection unit 3, and the tap position is stored in the storage unit 4 in advance as the determination data "c" in order to identify the tap position. Meanwhile, in the present exemplary embodiment, an association between a combination of the identified length of the vibration transmission path from the tap position and the arm posture based on the touched side detection unit 2, and the tap position is stored in the storage unit 4 as determination data "g" in advance.

In FIG. 19, the input device of the present exemplary embodiment comprises an input information identification unit 35, instead of the input information identification unit 5 (FIG. 1) in the input device of the first exemplary embodiment. Upon receiving the touched side detection data "p" and the touching side detection data "b," the input information identification unit 35 refers to the determination data "g" of the storage unit 4 and identifies the tap position from the length of the vibration transmission path and the arm posture at the touched side detection unit 2.

Next, an operation of the input device of the present exemplary embodiment will be described.

Figure 20:
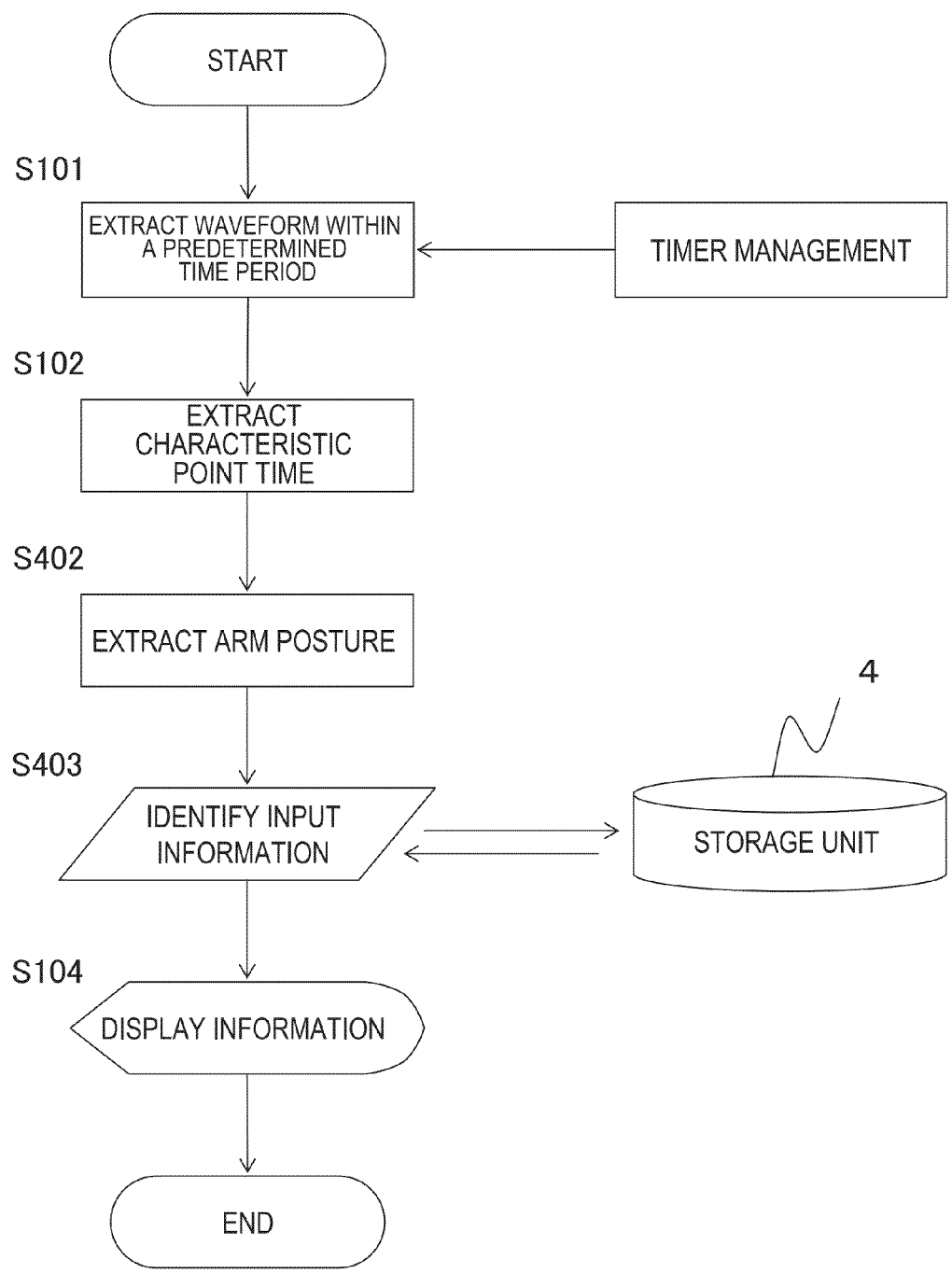
FIG. 20 is a flowchart showing an operation of the input device relating to the fourth exemplary embodiment.

FIG. 20 is a flowchart showing the operation of the input device relating to the present exemplary embodiment. The input device of the first exemplary embodiment extracts the characteristic point time in the step S102 of FIG. 5. Meanwhile, the input device of the present exemplary embodiment extracts the arm posture at the touched side detection unit 2 based on the touched side detection data "p" (step S402) after extracting the characteristic point time in the step S102.

Next, an operation of the input information identification unit 35 will be described in detail.

The input information identification unit 35 refers to the determination data "g" of the storage unit 4 that holds the association between the combination of the time difference due to the difference in the vibration transmission path from the tap position to each detection unit and the arm posture at the touched side detection unit 2, and the tap position, and identifies the tap position. As a result, the input information identification unit 35 identifies which input area, including the input areas 74 to 76 on the palm side of the arm shown in FIG. 18, is tapped and outputs the result as the input information identification data "d."

Next, the operation of the input information identification unit 35 in the step S402 will be described in detail.

The input information identification unit 35 extracts the arm posture using the direction of gravitational acceleration detected by the acceleration sensor 9 of the touched side detection unit 2 in the step S402.

Figure 21A:
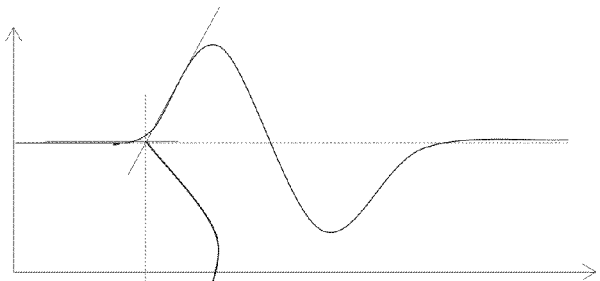
FIGS. 21A, 21B, and 21C are drawings for explaining vibration arriving time extraction and arm posture extraction performed by the input device relating to the fourth exemplary embodiment.
Figure 21B:
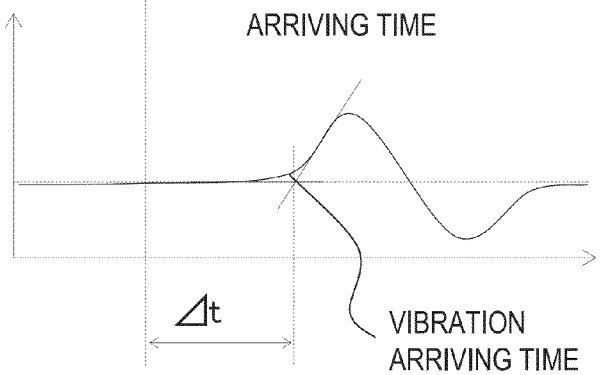
Figure 21C:
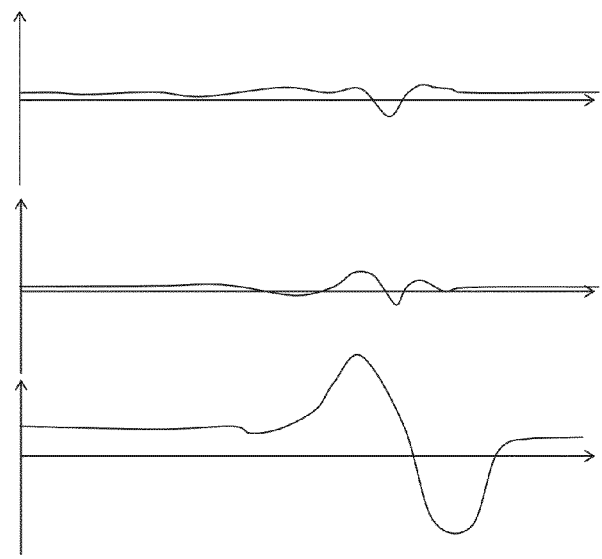

FIGS. 21A, 21B, and 21C are drawings for explaining the extraction of the vibration arriving time in the step S102 and the extraction of the arm posture in the step S402. FIGS. 21A and 21B are the same as FIGS. 7A and 7B. The extraction of the vibration arriving time in the step S102 is performed using the method described in the first exemplary embodiment. FIG. 21C shows a waveform of each component (the X, Y, and Z directions) of acceleration detected by the acceleration sensor 9 of the touched side detection unit 2. In FIG. 21C, a constant value is detected before the touched side detection unit 2 detects tapping impact. This indicates that constant gravitational acceleration is always exerted on the acceleration sensor 9. With reference to FIG. 21C, when an input operation is performed on the palm side of the arm as shown in FIG. 18, a positive value is detected as an acceleration component in the Z direction. Conversely, when an input operation is performed on the back side of the arm as shown in FIG. 2, a negative value is detected as an acceleration component in the Z direction. In the step S402, the input information identification unit 35 refers to the touched side detection data "p" shown in FIG. 21C and calculates the acceleration in a stationary state before the vibration arriving time as gravitational acceleration that should be associated with the arm posture.

Next, an operation of the input information identification unit 35 in step S403 will be described in detail.

FIG. 22 is a table showing the association between the combination of the lower and upper thresholds corresponding to the range of the length of the vibration transmission path from the tap position and the direction of gravitational acceleration corresponding to the arm posture included in the determination data "g" stored in the storage unit 4, and the input information identification data "d" as an example. The lower and upper thresholds are the same as those in FIG. 11 in the first exemplary embodiment. With reference to FIG. 22, the storage unit 4 holds the average values of the gravitational acceleration components (X, Y, Z) at each arm posture as the determination data "g" in order to express the directions of gravitational acceleration corresponding to the arm postures.

In the step S403, the determination data "g" stored in the storage unit 4 is referred to, the input area is identified by identifying the closest combination of the vibration transmission path length from the tap position included in the lower and upper thresholds and the acceleration detected as the gravitational acceleration expressing each arm posture, and data associating the input areas 71 to 76 therewith is deemed to be the determination data "g."

In the present exemplary embodiment, the input area is identified by calculating the length of the vibration transmission path from the tap position using the same method as that of the input device in the first exemplary embodiment and calculating the arm posture using gravitational acceleration, however, the method of the input device in the second or the third exemplary embodiment may be used as the method for calculating the vibration transmission path length from the tap position.

In the present exemplary embodiment, the input areas 74 to 76 are provided on the palm side of the arm. Similarly, new input areas may be provided on the radius side of the arm, which is a side on the arm.

Figure 23:
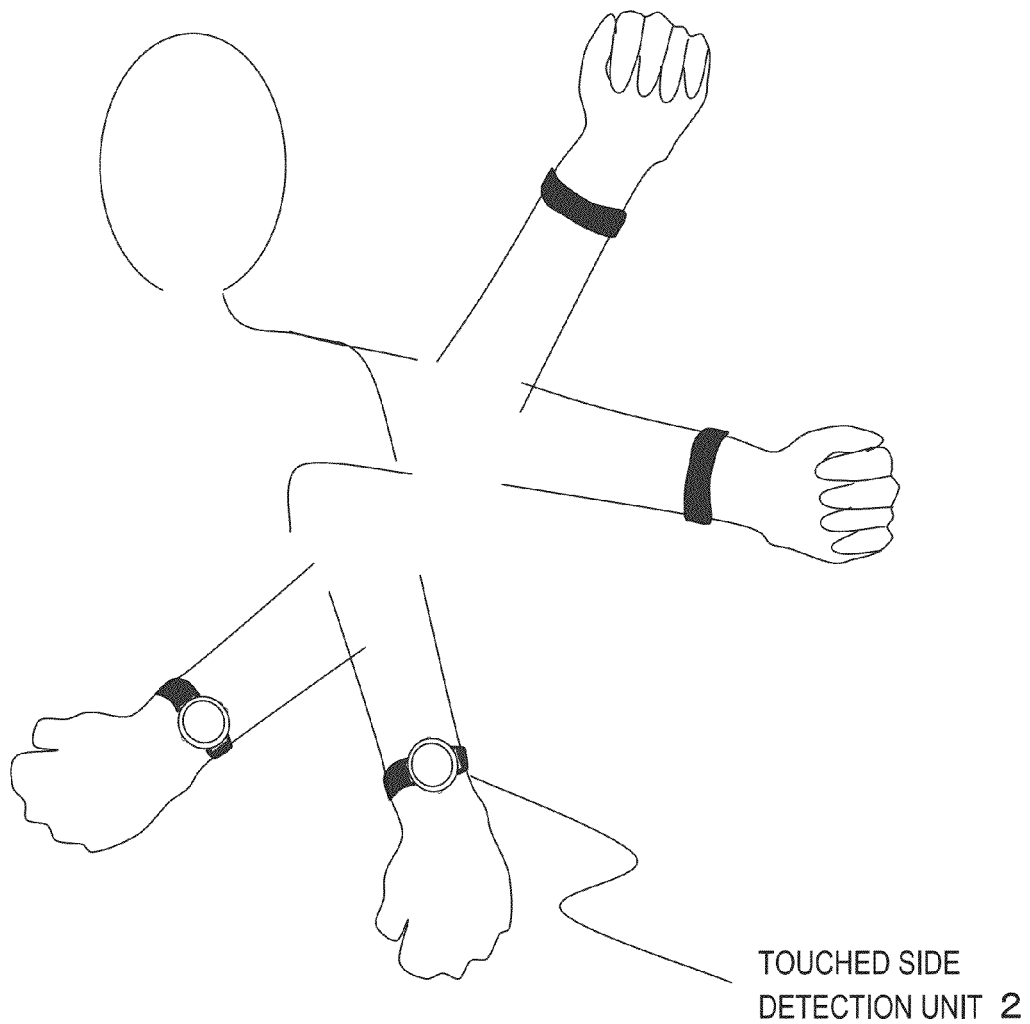
FIG. 23 is a drawing showing arm postures at the time of input operation in the input device relating to the fourth exemplary embodiment.

Further, FIG. 23 is a drawing showing arm postures at the time of input operation. With reference to FIG. 23, the input information identification data "d" may be changed according to each arm posture. For instance, the assigned operation command may be changed according to the arm posture such as raising the arm or lowering the arm when an input on the same input area 71 is detected.

Further, the assigned operation command may be changed according to changes in arm posture.

Further, in the present exemplary embodiment, the input area is identified by utilizing a gravitational acceleration to determine the arm posture using the acceleration sensor 9 to detect the arm posture, however, the arm posture may be determined by combining the acceleration sensor with other sensors such as an angle sensor or gyroscope.

By providing the acceleration sensor 9 in the touched side detection unit 2 as in the present exemplary embodiment, not only can the vibration transmission path length from the tap position be calculated from the amount of changes from a stationary state, but also the arm posture can be calculated by utilizing the gravitational acceleration. Therefore, according to the input device of the present exemplary embodiment, a plurality of state functions can be obtained without adding any sensor, and the configuration of the device can be simplified.

Modifications and adjustments of the exemplary embodiment are possible within the scope of the overall disclosure (including the claims) of the present invention and based on the basic technical concept of the present invention. Various combinations and selections of various disclosed elements (including each element of each claim, each element of each exemplary embodiment, each element of each drawing, etc.) are possible within the scope of the claims of the present invention. That is, the present invention of course includes various variations and modifications that could be made by those skilled in the art according to the overall disclosure including the claims and the technical concept.

Further, some or all of the exemplary embodiments above can be described as the appendixes below without being limited thereto.

(Appendix 1)

An input device comprising:

a detection unit that detects as detection data a vibration that is generated by tapping on a body of a user and transmitted through the body of the user; and an input information identification unit that refers to the detection data and that identifies a tap position based on a fact that the detection data varies according to a length of a vibration transmission path from the tap position to the detection unit.

(Appendix 2)

The input device according to Appendix 1, wherein the detection unit comprises a first detection unit provided on a tapping side and a second detection unit provided on a tapped side, and the input information identification unit identifies the tap position based on a difference between a time when the first detection unit detects the vibration and a time when the second detection unit detects the vibration.

(Appendix 3)

The input device according to Appendix 2, further comprising a storage unit that holds an association between a difference between a time when the first detection unit detects the vibration and a time when the second detection unit detects the vibration, and the tap position, wherein the input information identification unit identifies the tap position by referring to the storage unit.

(Appendix 4)

The input device according to Appendix 3, wherein the storage unit holds an association between upper and lower threshold values of a difference between a time when the first detection unit detects the vibration and a time when the second detection unit detects the vibration, and the tap position, and the input information identification unit identifies the tap position by determining whether or not the time difference detected is within a range between the upper and lower threshold values.

(Appendix 5)

The input device according to Appendix 1, wherein the detection unit comprises a first detection unit provided on a tapping side and a second detection unit provided on a tapped side, and the input information identification unit identifies the tap position based on a ratio between an amplitude, strength or energy of the vibration detected by the first detection unit and an amplitude, strength or energy of the vibration detected by the second detection unit.

(Appendix 6)

The input device according to Appendix 5, further comprising a storage unit that holds an association between a ratio between an amplitude, strength or energy of the vibration detected by the first detection unit and an amplitude, strength or energy of the vibration detected by the second detection unit, and the tap position, wherein the input information identification unit identifies the tap position by referring to the storage unit.

(Appendix 7

The input device according to Appendix 6, wherein the storage unit holds an association between upper and lower threshold values of a ratio between an amplitude, strength or energy of the vibration detected by the first detection unit and an amplitude, strength or energy of the vibration detected by the second detection unit, and the tap position, and the input information identification unit identifies the tap position by determining whether or not the ratio of the amplitude, strength or energy of the vibration detected is within a range between the upper and lower threshold values.

(Appendix 8)

The input device according to Appendix 1, wherein the detection unit is provided on a tapped side, and the input information identification unit identifies the tap position based on an amplitude, strength or energy of the vibration detected by the detection unit.

(Appendix 9)

The input device according to any one of Appendixes 1 to 8, wherein the input information identification unit outputs an operation command associated with the identified tap position.

(Appendix 10)

The input device according to any one of Appendixes 1 to 9, wherein the detection unit comprises an acceleration sensor that detects a vibration.

(Appendix 11)

An input method comprising:

by a computer, detecting as detection data a vibration that is generated by tapping on a body of a user and transmitted through the body of the user; and referring to the detection data and identifying a tap position based on a fact that the detection data varies according to a length of a vibration transmission path from the tap position to a detection place where the detection data is detected.

(Appendix 12)

The input method according to Appendix 11, wherein the computer identifies the tap position based on a difference between a time when the vibration is detected at a first detection place provided on a tapping side and a time when the vibration is detected at a second detection place provided on a tapped side.

(Appendix 13)

The input method according to Appendix 12, wherein the computer identifies the tap position by referring to a storage unit that holds an association between a difference between a time when the vibration is detected at the first detection place and a time when the vibration is detected at the second detection place, and the tap position.

(Appendix 14)

The input method according to Appendix 13, wherein the storage unit holds an association between upper and lower threshold values of a difference between a time when the vibration is detected at the first detection place and a time when the vibration is detected at the second detection place, and the tap position, and the computer identifies the tap position by determining whether or not the time difference detected is within a range between the upper and lower threshold values.

(Appendix 15)

The input method according to Appendix 11, wherein the computer identifies the tap position based on a ratio between an amplitude, strength or energy of the vibration detected at a first detection place provided on a tapping side and an amplitude, strength or energy of the vibration detected at a second detection place provided on a tapped side.

(Appendix 16)

The input method according to Appendix 15, wherein the computer identifies the tap position by referring to a storage unit that holds an association between a ratio between an amplitude, strength or energy of the vibration detected at the first detection place and an amplitude, strength or energy of the vibration detected at the second detection place, and the tap position.

(Appendix 17)

The input method according to Appendix 16, wherein the storage unit holds an association between upper and lower threshold values of a ratio between an amplitude, strength or energy of a vibration detected at the first detection place and an amplitude, strength or energy of the vibration detected at the second detection place, and the tap position, and the computer identifies the tap position by determining whether or not the ratio of the amplitude, strength or energy of the vibration detected is within a range between the upper and lower threshold values.

(Appendix 18)

The input method according to Appendix 11, wherein the computer identifies the tap position based on an amplitude, strength or energy of the vibration detected at the detection place provided on a tapped side.

(Appendix 19)

The input method according to any one of Appendixes 11 to 18, further comprising by the computer, outputting an operation command associated with the identified tap position.

(Appendix 20)

A program causing a computer to execute:

detecting as detection data a vibration that is generated by tapping on a body of a user and transmitted through the body of the user; and referring to the detection data and identifying a tap position based on a fact that the detection data varies according to a length of a vibration transmission path from the tap position to a detection place where the detection data is detected.

(Appendix 21)
The program according to Appendix 20, causing the computer to execute:
identifying the tap position based on a difference between a time when the vibration is detected at a first detection place provided on a tapping side and a time when the vibration is detected at a second detection place provided on a tapped side.

(Appendix 22)
The program according to Appendix 21, causing the computer to execute:
identifying the tap position by referring to a storage unit that holds an association between a difference between a time when the vibration is detected at the first detection place and a time when the vibration is detected at the second detection place, and the tap position.

(Appendix 23)
The program according to Appendix 22, wherein
the storage unit holds an association between upper and lower threshold values of a difference between a time when the vibration is detected at the first detection place and a time when the vibration is detected at the second detection place, and the tap position, and
the program causes the computer to execute identifying the tap position by determining whether or not the time difference detected is within a range between the upper and lower threshold values.

(Appendix 24)
The program according to Appendix 20, causing the computer to execute:
identifying the tap position based on a ratio between an amplitude, strength or energy of the vibration detected at a first detection place provided on a tapping side and an amplitude, strength or energy of the vibration detected at a second detection place provided on a tapped side.

(Appendix 25)
The program according to Appendix 24, causing the computer to execute:
identifying the tap position by referring to a storage unit that holds an association between a ratio between an amplitude, strength or energy of the vibration detected at the first detection place and an amplitude, strength or energy of the vibration detected at the second detection place, and the tap position.

(Appendix 26)
The program according to Appendix 25, wherein
the storage unit holds an association between upper and lower threshold values of a ratio between an amplitude, strength or energy of the vibration detected at the first detection place and an amplitude, strength or energy of the vibration detected at the second detection place, and the tap position, and
the program causes the computer to execute identifying the tap position by determining whether or not the ratio of the amplitude, strength or energy of the vibration detected is within a range between the upper and lower threshold values.

(Appendix 27)
The program according to Appendix 20, causing the computer to execute:
identifying the tap position based on an amplitude, strength or energy of the vibration detected at the detection place provided on a tapped side.

(Appendix 28)
The program according to any one of Appendixes 20 to 27, further causing the computer to execute:
outputting an operation command associated with the identified tap position.

(Appendix 29)
A computer-readable storage medium storing the program according to any one of Appendixes 20 to 28.

(Appendix 30)
The input device according to Appendix 1, wherein
the detection unit comprises an acceleration sensor, and
the input information identification unit identifies an arm posture on a tapped side according to a gravitational acceleration detected by the acceleration sensor and identifies the tap position based on the identified arm posture and on a fact that the detection data varies according to a length of the vibration transmission path from the tap position to the detection unit.

(Appendix 31)
The input device according to Appendix 30, wherein
the detection unit is provided on a wrist on a tapped side.

(Appendix 32)
The input device according to Appendix 30 or 31, wherein
the input information identification unit determines whether the arm posture on the tapped side is in a state in which a back of a hand is facing upward or downward according to the gravitational acceleration.

EXPLANATION OF SYMBOLS

1: detection unit
2: touched side detection unit
3: touching side detection unit
4: storage unit
5, 15, 25, 35: input information identification unit
6: information display unit
8: information display unit
9: acceleration sensor
10: wiring board
11: calculation processing unit
12: display content processing unit
13: display unit
14: casing
16: memory
71 to 76: input area
a, p: touched side detection data
b: touching side detection data
c, e, f, g: determination data
d: input information identification data
$L_0$ to $L_3$: distance

What is claimed is:
1. An input device, comprising:
a detection unit that includes acceleration sensors and detects a vibration that is generated by tapping on a body of a user and transmitted through the body of the user; and
an input information identification unit that refers to the vibration and identifies a tap position based on how the vibration varies according to a length of a transmission path of the vibration from the tap position to the detection unit,
wherein the detection unit comprises a first detection unit provided on a tapping side, the first detection unit comprising a first acceleration sensor among the acceleration sensors, and a second detection unit provided on a tapped side, the second detection unit comprising a second acceleration sensor among the acceleration sensors, and the input information identification unit identifies the tap position based on a difference between a time when the first detection unit detects the vibration and a time when the second detection unit detects the vibration.

2. The input device according to claim 1, further comprising a storage unit that holds an association between the difference between the time when the first detection unit detects the vibration and the time when the second detection unit detects the vibration, and the tap position, wherein the input information identification unit identifies the tap position by referring to the storage unit.

3. The input device according to claim 2, wherein the storage unit holds an association between upper and lower threshold values of the difference between the time when the first detection unit detects the vibration and the time when the second detection unit detects the vibration, and the tap position, and the input information identification unit identifies the tap position by determining whether or not the time difference detected is within a range between the upper and lower threshold values.

4. The input device according to claim 1, wherein the input information identification unit identifies the tap position based on a ratio between an amplitude, strength or energy of the vibration detected by the first detection unit and an amplitude, strength or energy of the vibration detected by the second detection unit.

5. The input device according to claim 4, further comprising:

a storage unit that holds an association between a ratio between an amplitude, strength or energy of the vibration detected by the first detection unit and an amplitude, strength or energy of the vibration detected by the second detection unit, and the tap position, wherein the input information identification unit identifies the tap position by referring to the storage unit.

6. The input device according to claim 5, wherein the storage unit holds an association between upper and lower threshold values of the ratio between the amplitude, strength or energy of the vibration detected by the first detection unit and the amplitude, strength or energy of the vibration detected by the second detection unit, and the tap position, and the input information identification unit identifies the tap position by determining whether or not the ratio of the amplitude, strength or energy of the vibration detected is within a range between the upper and lower threshold values.

7. The input device according to claim 1, wherein the input information identification unit identifies the tap position based on an amplitude, strength or energy of the vibration detected by the detection unit.

8. The input device according to claim 1, wherein the input information identification unit identifies an arm posture on a tapped side according to a gravitational acceleration detected by one of the acceleration sensors and identifies the tap position based on the identified arm posture and based on how the vibration varies according to the length of the transmission path of the vibration from the tap position to the detection unit.

9. The input device according to claim 8, wherein the second detection unit is provided on a wrist on the tapped side.

10. The input device according to claim 8, wherein the input information identification unit determines whether the arm posture on the tapped side is in a state in which a back of a hand is facing upward or downward according to the gravitational acceleration.

11. An input method, comprising:

detecting, by a processor of a computer, a vibration that is generated by tapping on a body of a user and transmitted through the body of the user; and referring to the vibration and identifying a tap position based on how the vibration varies according to a length of a transmission path of the vibration from the tap position to a detection place where the vibration is detected, wherein the detecting the vibration comprises detecting the vibration using a first detection unit provided on a tapping side, the first detection unit comprising a first acceleration sensor, and using a second detection unit provided on a tapped side, the second detection unit comprising a second acceleration sensor, and the identifying the tap position comprises identifying the tap position based on a difference between a time when the first detection unit detects the vibration and a time when the second detection unit detects the vibration.

12. The input method according to claim 11, wherein the processor identifies the tap position based on a ratio between an amplitude, strength or energy of the vibration detected at a first detection place provided on the tapping side and an amplitude, strength or energy of the vibration detected at a second detection place provided on the tapped side.

13. A non-transitory computer-readable storage medium storing a program that causes a processor of a computer to execute:

detecting a vibration that is generated by tapping on a body of a user and transmitted through the body of the user; and referring to the vibration and identifying a tap position based on how the vibration varies according to a length of a transmission path of the vibration from the tap position to a detection place where the vibration is detected, wherein the detecting the vibration comprises detecting the vibration using a first detection unit provided on a tapping side, the first detection unit comprising a first acceleration sensor, and using a second detection unit provided on a tapped side, the second detection unit comprising a second acceleration sensor, and the identifying the tap position comprises identifying the tap position based on a difference between a time when the first detection unit detects the vibration and a time when the second detection unit detects the vibration.

14. The medium according to claim 13, wherein the program causes the processor to execute:

identifying the tap position based on a ratio between an amplitude, strength or energy of the vibration detected at a first detection place provided on the tapping side and an amplitude, strength or energy of the vibration detected at a second detection place provided on the tapped side.

* * * * *